United States Patent
Wu et al.

(10) Patent No.: US 7,468,419 B2
(45) Date of Patent: Dec. 23, 2008

(54) CYCLOSPORIN DERIVATIVES FOR THE TREATMENT OF IMMUNE DISORDERS

(75) Inventors: Frank X. H. Wu, Shrewsbury, MA (US); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 11/765,261

(22) Filed: Jun. 19, 2007

(65) Prior Publication Data

US 2007/0249527 A1 Oct. 25, 2007

Related U.S. Application Data

(63) Continuation of application No. 10/600,303, filed on Jun. 20, 2003, now abandoned.

(51) Int. Cl.
*A61K 38/12* (2006.01)
(52) U.S. Cl. .......................................... 530/317; 514/11
(58) Field of Classification Search ................. 530/317; 514/11
See application file for complete search history.

(56) References Cited

OTHER PUBLICATIONS

Durette P. L., (Transplantation Proceedings 20(2), Suppl 2, 51-57, 1988).*
Colombani P M (Transplantation Proceedings 20(2), Suppl 2, 46-50, 1988).*
Benson (Transplantation 47(4), 696-703, 1989).*
Kallen J. (Journal of Molecular Biology 283(2) 435-49, 1998).*
Ruiz F. (Euro J. Pharmacol. 404(1-2) 29-39, 2000).*
Bendtzen K. (Scand. J. Immunol. 20(1) 43-51, 1984).*
Hartman (Biochem Biophys Res Commun 133(3) 964-71, 1985).*
Silverman (Antimicrobial Agents Chemother 41(9) 1859-66 1997).*
Izawa, A. (Transplantation Proceedings 36(2S), 570S-573S, 2004).*
Halloran, P. F. (Transplantation Proceedings 33(7-8), 3067-3069, 2001).*
Sigal, N. (J. Exp. Med. 173, 619-628, 1991).*
Ullrich, Volker (Toxicology Letters 139(2-3), 107-110, 2003).*
Jose, Matthew (Nephrology 12(Suppl. 1), S66-S74, 2007).*

* cited by examiner

*Primary Examiner*—David Lukton
(74) *Attorney, Agent, or Firm*—Carolyn S. Elmore; Edgar W. Harlan; Elmore Patent Law Group

(57) ABSTRACT

The present invention relates to a cyclosporin analog of the following formula (I) or a pro-drug or pharmaceutically acceptable salt thereof:

$$\begin{array}{l} \text{N(Me)CH(A)C(O)----B---Sar-MeLeu-Val-MeLeu-Ala-----} \\ \phantom{\text{N(Me)CH(A)C(O)----}} 1 \phantom{\text{---}} 2 \phantom{\text{---}} 3 \\ \phantom{\text{N(Me)CH(A)C(O)----B---}} \text{U---MeLeu-MeLeu-MeVal} \\ \phantom{\text{N(Me)CH(A)C(O)----B---}} 8 \phantom{\text{MeLeu-}} 11 \end{array} \quad (I)$$

wherein
A is of the formula:

where Q, W, X, Y, and Z are defined herein. In a second embodiment, the present invention relates to pharmaceutical compositions comprising pro-drugs or pharmaceutically acceptable salts of the compounds of the present invention and the use thereof for treating autoimmune diseases or for the prevention of organ transplantation rejection in a subject. In a third embodiment, the present invention relates to processes for the production of novel cyclosporin analogs of the present invention.

8 Claims, No Drawings

CYCLOSPORIN DERIVATIVES FOR THE TREATMENT OF IMMUNE DISORDERS

RELATED APPLICATION

This application is a continuation of U.S. application Ser. No. 10/600,303, filed Jun. 20, 2003 now abandoned. The entire teachings of the above application are incorporated herein by reference.

TECHNICAL FIELD

The present invention relates to novel semisynthetic cyclosporin analogs for the prevention of organ transplantation rejection and the treatment of immune disorders and inflammation, their use as pharmaceuticals and pharmaceutical compositions comprising them, as well as the processes for their production.

BACKGROUND OF THE INVENTION

The cyclosporins comprise a class of structurally distinctive, cyclic, poly-N-methylated undecapeptides, commonly possessing pharmacological, in particular immunosuppressive, anti-inflammatory and antiparasitic activity. The first of the cyclosporins to be isolated was the naturally occurring fungal metabolite Ciclosporin or Cyclosporin, also known as cyclosporin A.

Since the original discovery of Cyclosporin, a wide variety of naturally occurring cyclosporins have been isolated and identified, and many further non-natural cyclosporins have been prepared by total- or semi-synthetic means or by the application of modified culture techniques. The class comprised by the cyclosporins is thus now substantial and includes, for example, the naturally occurring cyclosporins A through Z [cf., Traber et al.; 1, Helv. Chim. Acta, 60, 1247-1255 (1977); Traber et al.; 2, Helv. Chim. Acta, 65, 1655-1667 (1982); Kobel et al.; Europ. J. Applied Microbiology and Biotechnology, 14, 273-240 (1982); and von Wartburg et al.; Progress in Allergy, 38, 28-45 (1986)], as well as various non-natural cyclosporin derivatives and artificial or synthetic cyclosporin derivatives and artificial or synthetic cyclosporins including dihydrocyclosporins [in which the -MeBmt-residue is saturated by hydrogenation]; derivatized cyclosporins (e.g., in which the 3'-O-atom of the -MeBmt-residue is acylated or a further substituent is introduced at the α-carbon atom of the sarcosyl residue at the 3-position); and cyclosporins in which variant amino acids are incorporated at specific positions within the peptide sequence, e.g. employing the total synthetic method for the production of cyclosporins developed by R. Wenger—see e.g. Traber et al., 1; Traber et al., 2; and Kobel et al., loc cit. U.S. Pat. Nos. 4,108,985, 4,220,641, 4,288,431, 4,554,351, 4,396,542 and 4,798,823; European Patent Publication Nos. 34,567A, 56,782A, 300, 784A and 300,785; International Patent Publication No. WO 86/02080 and UK Patent Publication Nos. 2,206,119 and 2,207,678; Wenger 1, Transpl. Proc., 15 Suppl. 1:2230 (1983); Wenger 2, Angew. Chem. Int. Ed. 24 77 (1985) and Wenger 3, Progress in the Chemistry of Organic Natural Products, 50, 123 (1986).

Several synthetic modifications of the -MeBmt-residue residing at position 1 of the cyclosporin undecapeptide have been described including: Park et al., *Tetrahedron Lett.* 1989, 30, 4215-4218; U.S. Pat. Nos. 5,239,037, 5,293,057; U.S. Publication Nos. US20020142946, US20030087813, and US20030104992 assigned to Enanta Pharmaceuticals, Inc.; PCT Publication Nos. WO99/18120 and WO03/033526 both assigned to Isotechnika; and U.S. Pat. Nos. 4,384,996, 4,771, 122, 5,284,826, and 5,525,590 assigned to Sandoz.

The compound cyclosporine (cyclosporine A or CsA) has found wide use since its introduction in the fields of organ transplantation and immunomodulation, and has brought about a significant increase in the success rate for transplantation procedures. Undesired side effects associated with cyclosporine, however, such as nephrotoxicity, have led to a continued search for immunosuppressant compounds having improved, efficacy and safety.

Side effects with systemic CsA include increase in diastolic blood pressure and decrease in renal function. Other side effects include hepatic dysfunction, hypertrichosis, tremor,

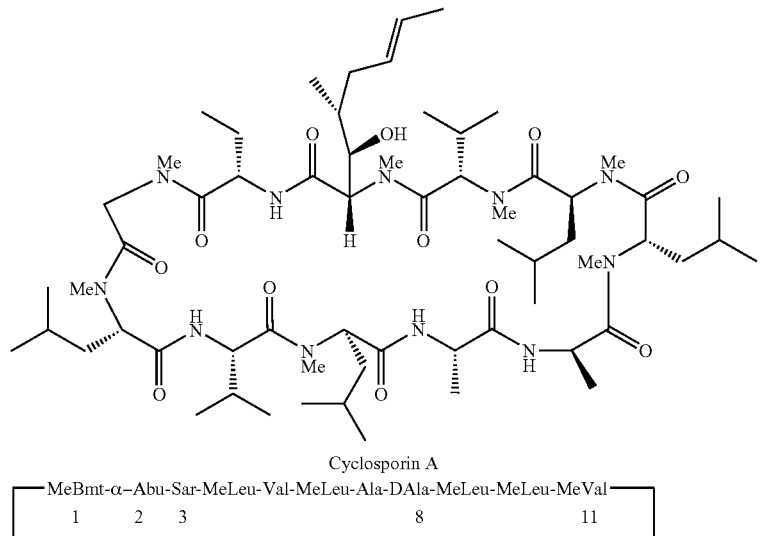

Cyclosporin A

MeBmt-α-Abu-Sar-MeLeu-Val-MeLeu-Ala-DAla-MeLeu-MeLeu-MeVal
1    2   3              8              11 gingival hyperplasis and paraesthsia. The systemic toxicity of CsA limits its use for the treatment of certain diseases. Accordingly, a need exists for compounds which exhibit immunosuppressive activity while not producing systemic toxicity.

SUMMARY OF THE INVENTION

The present invention relates to novel cyclosporin analogs and methods of treatment for the prevention of organ transplantation rejection and the treatment of immune disorders or inflammation in a subject. The present invention further relates to pharmaceutical compositions comprising the compounds of the present invention and processes for their production.

More particularly, the present invention provides a cyclosporin of the following Formula (I),

(I)

wherein
A is of the formula:

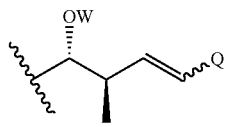

wherein:
Q is

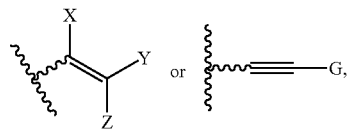

where
i) X is selected from hydrogen, halogen, $C_1$-$C_6$ alkyl, or aryl;
ii) one of Y and Z is selected from: hydrogen, deuterium, halogen, or methyl and the other is independently selected from:
  a) halogen;
  b) $R_1$, where $R_1$ is selected from:
    1) hydrogen;
    2) deuterium;
    3) $C_1$-$C_6$ alkyl, optionally substituted with halogen, TMS, aryl, heterocycloalkyl, or heteroaryl;
    4) $C_2$-$C_6$ alkenyl, optionally substituted with halogen, TMS, aryl, heterocycloalkyl, or heteroaryl;
    5) $C_2$-$C_6$ alkynyl, optionally substituted with halogen, TMS, aryl, heterocycloalkyl, or heteroaryl;
    6) $C_3$-$C_{12}$ cycloalkyl;
    7) substituted $C_3$-$C_{12}$ cycloalkyl;
    8) aryl;
    9) substituted aryl;
    10) heterocycloalkyl;
    11) substituted heterocycloalkyl;
    12) heteroaryl; or
    13) substituted heteroaryl;
  c) —C(O)$OR_1$, where $R_1$ is as previously defined;
  d) —C(O)OCH$_2$—V—$R_1$, where $R_1$ is as previously defined and V is —O— or —S—;
  e) —C(O)N($R_3$)($R_4$), where $R_3$ and $R_4$ are independently selected from $R_1$ as previously defined;
  f) —C(O)$SR_1$, where $R_1$ is as previously defined;
  g) —C(O)OCH$_2$OC(O)$R_1$, where $R_1$ is as previously defined;
  h) —C(S)$OR_1$, where $R_1$ is as previously defined;
  i) —C(S)$SR_1$, where $R_1$ is as previously defined;
  j) $R_2$, where $R_2$ is selected from:
    1) $C_1$-$C_6$ alkyl-M-$R_1$, where $R_1$ is as previously defined and M is absent or selected from:
      i. —NH—;
      ii. —N(CH$_3$)—;
      iii. —S—;
      iv. —S(O)$_n$—, where n=0, 1, or 2; or
      v. —O—;
    2) $C_2$-$C_6$ alkenyl-M-$R_1$, where $R_1$ and M are as previously defined; or
    3) $C_2$-$C_6$ alkynyl-M-$R_1$, where $R_1$ and M are as previously defined;
  k) Or in the alternative, Y and Z are taken together with the carbon atom to which they are attached to form a $C_3$-$C_{12}$ cycloalkyl moiety; and
  ii) G is independently selected from halogen, TMS, $R_1$ or $R_2$ as previously defined;
B is selected from:
  i) -αAbu-;
  ii) -Val-;
  iii) -Thr-; or
  iv) -Nva-;
U is selected from:
  i) -(D)Ala-;
  ii) -(D)Ser-;
  iii) -[O-(2-hydroxyethyl)(D)Ser]-;
  iv) -[O-(acyl)(D)Ser]-; or
  v) -[O-(2-acyloxyethyl)(D)Ser]-; and
W is selected from hydrogen or a hydroxy protecting group.

In Formula (I), amino acid residues referred to by abbreviation, e.g. -Ala-, -MeLeu-, -αAbu-, etc., are, in accordance with conventional practice, to be understood as having the L-configuration unless otherwise indicated. (For example, -(D)Ala-represents a residue having the D-configuration). Residue abbreviation preceeded by "Me" as in the case of "MeLeu," represents an α-N-methylated residue. Individual residues of the cyclosporin molecule are numbered, as in the art, clockwise and starting with the residue, -MeBmt-corresponding to residue 1. The same numerical sequence is employed throughout the present specifications and claims.

Accordingly, the present invention provides the use of cyclosporin analogs for the treatment of, with or without the concurrent use of other drugs, organ transplantation rejections, immune disorders, and inflammation including, but not limited to, indications such as rheumatoid arthritis, psoriasis, inflammatory bowel diseases, chronic obstructive pulmonary disease, allergic rhinitis, and asthma.

DETAILED DESCRIPTION OF THE INVENTION

A first embodiment of the invention is a compound represented by Formula I as described above, or a pharmaceutically acceptable salt, ester or prodrug thereof.

Representative subgenera of the present invention include, but are not limited to, the following:

A compound of formula I: A is of the formula A1:

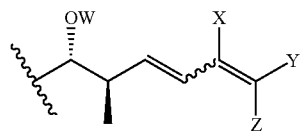
(A1)

where W, X, Y, and Z are as previously defined;

A compound of formula I: A is of the formula A2:

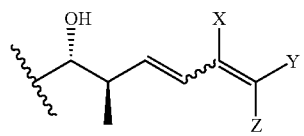
(A2)

where X, Y, and Z are as previously defined;

A compound of formula I: A is of the formula A3:

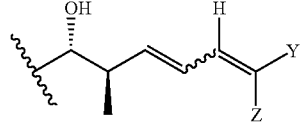
(A3)

where Y and Z are as previously defined;

A compound of formula I: A is of the formula A4:

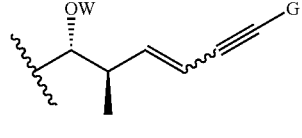
(A4)

where W and G are as previously defined; or

A compound of formula I: A is of the formula A5:

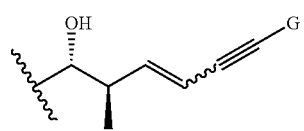
(A5)

G is as previously defined.

Representative compounds of the invention include, but are not limited to, the compounds selected from:

Example 1. A compound of formula I, wherein A is of the formula (1-2) and W is Ac;

Example 2. A compound of formula I, wherein Q is

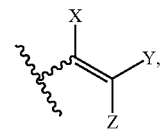

W is Ac and X=Y=Z hydrogen;

Example 3. A compound of formula I, wherein Q is

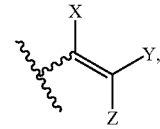

W is H and X=Y=Z=hydrogen;

Example 4. A compound of formula I, wherein Q is

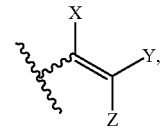

Y is $CH_3$, and W=X=Z=hydrogen;

Example 5. A compound of formula I, wherein Q is

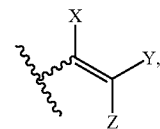

Y=Z=$CH_3$, and W=X=hydrogen;

Example 6. A compound of formula I, wherein Q is

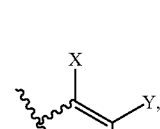

Y is —$(CH_2)_3CH_3$, and W=X=Z=hydrogen;

Example 7. A compound of formula I, wherein Q is

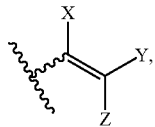

Y is —(CH$_2$)$_2$Br, and W=X=Z=hydrogen;

Example 8. A compound of formula I, wherein Q is

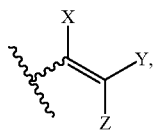

Y is ortho-Me-phenyl, and W=X=Z=hydrogen;

Example 9. A compound of formula I, wherein Q is

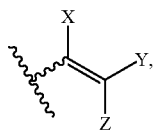

Y is ortho-Br-phenyl, and W=X=Z=hydrogen;

Example 10. A compound of formula I, wherein Q is

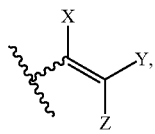

Y is —CO$_2$Me, and W=X=Z=hydrogen;

Example 11. A compound of formula I, wherein Q is

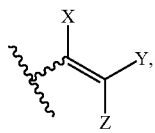

Y is meta-CHO-phenyl, and W=X=Z=hydrogen;

Example 12. A compound of formula I, wherein Q is

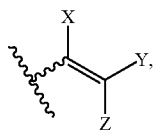

Y is Et, and W=X=Z=hydrogen;

Example 13. A compound of formula I, wherein Q is

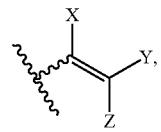

Y is —CH═CHCH$_2$TMS, and W=X=Z=hydrogen;

Example 14. A compound of formula I, wherein Q is

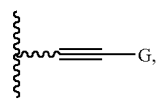

G is H, and W is H.

Example 15. A compound of formula I, wherein Q is

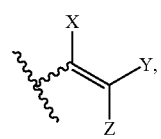

Y is propyl, and W=X=Z=hydrogen.

Example 16. A compound of formula I, wherein Q is

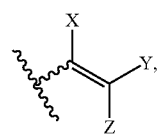

Y is cyclopropyl, and W=X=Z=hydrogen.

Example 17. A compound of formula I, wherein Q is

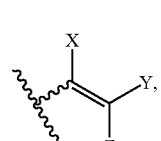

Y is —CH═CHCH$_3$, and W=X=Z=hydrogen.

Example 18. A compound of formula I, wherein Q is

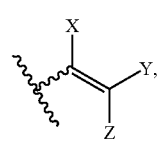

X=Y=CH$_3$, and W Z=hydrogen.

Example 19. A compound of formula I, wherein Q is

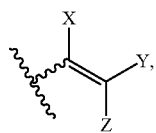

W=X=Y=hydrogen, and Z=CH$_3$.

Example 20. A compound of formula I, wherein Q is

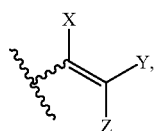

Y is p-bromophenyl, and W=X=Z=hydrogen.

Example 21. A compound of formula I, wherein Q is

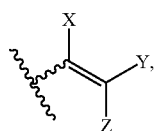

W=X=Y=hydrogen, and Z=—CH$_2$CH=CH$_2$.

Example 22. A compound of formula I, wherein Q is

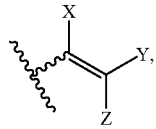

W=X=Y=hydrogen, and Z is ethyl.

Example 23. A compound of formula I, wherein Q is

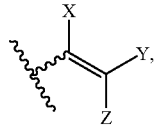

W=X=Y=hydrogen, and Z=—CH=CHCH$_3$.

Example 24. A compound of formula I, wherein Q is

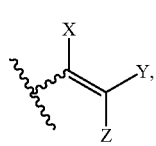

W=X=Y=hydrogen, and Z=—CH$_2$OCH$_3$.

Example 25. A compound of formula I, wherein Q is

G=—CH=CHCH$_3$ and W=hydrogen.

Example 26. A compound of formula I, wherein Q is

G=propyl and W=hydrogen.

Example 27. A compound of formula I, wherein Q is

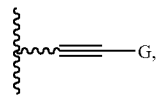

G=—CH$_3$ and W=hydrogen.

The potent immunomodulatory activity which compounds of the instant invention demonstrate in common in vitro biological assays (for example, calcineurin phosphatase and binding assays, nuclear factor of activated T cells (NFAT) reporter gene assay, murine and human mixed lymphocyte reaction) or animal models (for example delayed-type hypersensitivity response—DTH, -allergan induced pulmonary eosinophilia) indicate that these compounds possess immunosuppressive, antimicrobial, antifungal, antiviral, antiinflammatory, and antiproliferative activity, and possess the ability to reverse chemotherapeutic drug resistance. As agents block T-cell activation, a prerequisite for human immunodeficiency virus (HIV) proliferation, the compounds are useful as prophylactics for the prevention of HIV replication. The compounds of the invention would be useful when used alone, or in combination therapy with other immunosuppressants, for example, but not limited to, FK506, rapamycin, cyclosporin A, picibanil, mycophenolic acid, azathioprine, prednisolone, cyclophosphamide, brequinar and leflunomide.

As immunosuppressants, the compounds of the present invention are useful when administered for the prevention of immune-mediated tissue or organ graft rejection. Examples of transplanted tissues and organs which suffer from these effects are heart, kidney, liver, medulla ossium, skin, cornea, lung, pancreas, intestinum tenue, limb, muscle, nervus, duodenum, small-bowel, pancreatic-islet-cell, and the like; as well as graft-versus-host diseases brought about by medulla ossium transplantation. The regulation of the immune response by the compounds of the invention would also find utility in the treatment of autoimmune diseases, such as rheumatoid arthritis, systemic lupus erythematosis, hyperimmunoglobulin E, Hashimoto's thyroiditis, multiple sclerosis, progressive systemic sclerosis, myasthenia gravis, type I diabetes, uveitis, allergic encephalomyelitis, glomerulonephritis, and the like; and further infectious diseases caused by pathogenic microorganisms, such as HIV. In the particular cases of HIV-1, HIV-2 and related retroviral strains, inhibition of T-cell mitosis would suppress the replication of the virus, since the virus relies upon the host T-cell's proliferative functions to replicate.

Further uses include the treatment and prophylaxis of inflammatory and hyperproliferative skin diseases and cutaneous manifestations of immunologically-mediated illnesses, such as psoriasis, atopical dermatitis, contact dermatitis and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne and Alopecia greata; various eye diseases (autoimmune and otherwise) such as keratoconjunctivitis, vernal conjunctivitis, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, multiple myeloma, etc.; obstructive airway diseases, which includes conditions such as chronic obstructive pulmonary disease (COPD), asthma (for example, bronchial asthma, allergic asthma, intrinsic asthma, extrinsic asthma and dust asthma), particularly chronic or inveterate asthma (for example, late asthma and airway hyper-responsiveness), bronchitis, allergic rhinitis and the like; inflammation of mucosa and blood vessels such as gastric ulcers, vascular damage caused by ischemic diseases and thrombosis. Moreover, hyperproliferative vascular diseases such as intimal smooth muscle cell hyperplasia, restenosis and vascular occlusion, particularly following biologically- or mechanically-mediated vascular injury can be treated or prevented by the compounds of the invention.

Other treatable conditions would include, but are not limited to, ischemic bowel diseases, inflammatory bowel diseases, necrotizing enterocolitis, intestinal lesions associated with thermal burns and leukotriene $B_4$-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastro-intestinal tract (e.g., migraine, rhinitis and eczema); renal diseases such as interstitial nephritis, Goodpasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fasciitis; periodontal disease such as lesions of gingiva, periodontium, alveolar bone and substantia ossea dentis; nephrotic syndrome such as glomerulonephritis; male pattern aleopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infraction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-$C_4$ release; Behcet's disease such as intestinal-, vasculo- or neuro-Behcet's disease, and also Behcet's which affects the oral cavity, skin, eye, vulva, articulation, epididymis, lung, kidney and so on.

Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g., necrosis caused by toxin, viral hepatitis, shock or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmention of chemotherapeutic effect, preventing or treating activity of cytomegalovirus infection, particularly human cytomegalovirus (HCMV) infection, anti-inflammatory activity, and so on.

The compounds of the present invention may be used as vaccines to treat immunosuppression in a subject. It is sometimes found that the antigen introduced into the body for the acquisition of immunity from disease also acts as an immunosuppressive agent, and therefore, antibodies are not produced by the body and immunity is not acquired. By introducing a compound of the present invention into the body as a vaccine, the undesired immunosuppression may be overcome and immunity acquired.

The compounds of the present invention may also find utility in the chemosensitization of drug resistant target cells. Cyclosporin A and FK-506 are known to be effective modulators of P-glycoprotein, a substance which binds to and inhibits the action of anticancer drugs by inhibiting P-glycoprotein, as they are capable of increasing the sensitivity of multidrug resistant (MDR) cells to chemotherapeutic agents. It is believed that the compounds of the invention may likewise be effective at overcoming resistance expressed to clinically useful antitumour drugs such as 5-fluorouracil, cisplatin, methotrexate, vincristine, vinblastine and adriamycin, colchicine and vincristine.

Further, it has recently been shown that the steroid receptor-associated heat shock proteins (hsp), hsp56 or hsp59, belong to the class of immunophilin proteins (see "HSP70 induction by cyclosporin A in cultured rat hepatocytes: effect of vitamin E succinate," Andres, David et al., *Instituto de Bioqimica, Facultad de Farmacia, Universidad Complutense, Madrid, Spain*. J. Hepatol. (2000) 33(4), 570-579; "Cyclosporin A Induces an Atypical Heat Shock Response," Paslaru, Liliana, et al., Unite de Genetique Moleculaire, Paris, Fr. Biochem. Biophys. Res. Commun. (2000), 269(2), 464-469; "The cyclosporine A -binding immunophilin CyP-40 and the FK506-binding immunophilin hsp56 bind to a common site on hsp90 and exist in independent cytosolic heterocomplexes with the untransformed glucocorticoid receptor," Owens-Grillo, Janet K. et al., Med. Sch., Univ. Michigan, Ann Arbor, Mich. USA. J. Biol. Chem. (1995), 270(35), 20479-84). The ability of a steroid receptor-associated heat shock protein to bind the immunosuppressive CsA suggests that the steroid receptor and immunophilin signal transduction pathways are functionally interrelated. The combined treatment of compounds of the present invention and low concentrations of a steroid ligand (for e.g., progesterone, dexamethasone) result in a significant enhancement of target gene expression over that seen in response to ligand alone. Thus, the compounds of the present invention potentiate steroid-mediated transactivation.

Aqueous liquid compositions of the present invention may be particularly useful for the treatment and prevention of various diseases of the eye such as autoimmune diseases (including, for example, conical cornea, keratitis, dysophia epithelialis corneae, leukoma, Mooren's ulcer, sclevitis and Graves' opthalmopathy) and rejection of corneal transplantation.

Accordingly, the pharmaceutical compositions of the present invention comprise a therapeutically effective amount of a cyclosporin analog of the invention (e.g. those of the formulae delineated herein) in combination with a pharmaceutically acceptable carrier or excipient. In particular, compositions pertaining to the present invention are useful for treating a subject for immune-mediated organ or tissue allograft rejection, a graft-versus-host disease, an autoimmune disease, an obstructive airway disease, a hyperproliferative disease, or an ischemic or inflammatory intestinal or bowel disease.

The present invention also relates to method(s) of treatment of immune disorders and inflammation or prevention of organ transplant rejection in a subject by administering to the subject therapeutically effective amounts of the cyclosporin analogs of the present invention with or without the concurrent use of other drugs or pharmaceutically acceptable excipients, as described throughout the present specification.

The methods of the present invention comprise treating a subject in need of immunosuppresive, anti-inflammatory, antimicrobial, antifungal, antiviral or antiproliferative therapy, or requiring the reversal of chemotherapeutic drug resistance, by administering a therapeuticaly effective amount of a compound of the invention for such time and in such amounts as is necessary to produce the desired result.

The method includes administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

Also within the scope of this invention is a packaged product. The packaged product includes a container, one of the aforementioned compounds in the container, and a legend (e.g., a label or an insert) associated with the container and indicating administration of the compound for treating a disorder associated with bacterial infection, including the diseases delineated herein.

The present invention also contemplates processes to make any cyclosporin derivative delineated herein via any synthetic method delineated herein.

Definitions

Listed below are definitions of various terms used to describe this invention. These definitions apply to the terms as they are used throughout this specification and claims, unless otherwise limited in specific instances, either individually or as part of a larger group.

The terms "$C_1$-$C_3$ alkyl," "$C_1$-$C_6$ alkyl," or "$C_1$-$C_{12}$ alkyl," as used herein, refer to saturated, straight- or branched-chain hydrocarbon radicals containing between one and three, one and twelve, or one and six carbon atoms, respectively. Examples of $C_1$-$C_3$ alkyl radicals include methyl, ethyl, propyl and isopropyl radicals; examples of $C_1$-$C_6$ alkyl radicals include, but are not limited to, methyl, ethyl, propyl, isopropyl, n-butyl, tert-butyl, neopentyl and n-hexyl radicals; and examples of $C_1$-$C_{12}$ alkyl radicals include, but are not limited to, ethyl, propyl, isopropyl, n-hexyl, octyl, decyl, dodecyl radicals.

The term "substituted alkyl," as used herein, refers to a "$C_2$-$C_{12}$ alkyl" or "$C_1$-$C_6$ alkyl" group as previously defined, substituted by independent replacement or one, two, or three of the hydrogen atoms thereon with substituents including, but not limited to, —F, —Cl, —Br, —I, —OH, protected hydroxy, —$NO_2$, —CN, —$C_1$-$C_{12}$-alkyl optionally substituted with halogen, $C_2$-$C_{12}$-alkenyl optionally substituted with halogen, —$C_2$-$C_{12}$-alkynyl optionally substituted with halogen, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_2$-$C_{12}$-alkyl, —$C_2$-$C_{12}$-alkenyl, —O—$C_2$-$C_{12}$-alkenyl, —O—$C_3$-$C_{12}$-cycloalkyl, —O-aryl, —O-heteroaryl, -O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$—$C_3$-$C_{12}$-alkyl, —$OCO_2$—$C_2$-$C_{12}$-alkenyl, —$OCO_2$—$C_2$-$C_{12}$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkenyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

The terms "C$_2$-C$_{12}$ alkenyl" or "C$_2$-C$_6$ alkenyl," as used herein, denote a monovalent group derived from a hydrocarbon moiety containing from two to twelve or two to six carbon atoms having at least one carbon-carbon double bond. Alkenyl groups include, but are not limited to, for example, ethenyl, propenyl, butenyl, 1-methyl-2-buten-1-yl, 3-hexenyl, and the like.

The term "substituted alkenyl," as used herein, refers to a "C$_2$-C$_{12}$ alkenyl" or "C$_2$-C$_6$ alkenyl" group as previously defined, substituted by independent replacement or one, two, or three of the hydrogen atoms thereon with substituents including, but not limited to, —F, —Cl, —Br, —I, —OH, protected hydroxy, —NO$_2$, —CN, —C$_1$-C$_{12}$-alkyl optionally substituted with halogen, C$_2$-C$_{12}$-alkenyl optionally substituted with halogen, —C$_2$-C$_{12}$-alkynyl optionally substituted with halogen, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_1$-C$_{12}$-alkyl, -O—C$_2$-C$_{12}$-alkenyl, —O—C$_2$-C$_{12}$-alkenyl, —O—C$_3$-C$_{12}$-cycloalkyl, —O-aryl, —O-heteroaryl, -O-heterocycloalkyl, —C(O)—C$_1$-C$_{12}$-alkyl, —C(O)—C$_2$-C$_{12}$-alkenyl, —C(O)—C$_2$-C$_{12}$-alkenyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkenyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkenyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkenyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkenyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkenyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$-C$_{12}$-alkyl, —NHC(O)NH—C$_2$-C$_{12}$-alkenyl, —NHC(O)NH—C$_2$-C$_{12}$-alkenyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, NHC(S)NH—C$_1$-C$_{12}$-alkyl, —NHC(S)NH—C$_2$-C$_{12}$-alkenyl, —NHC(S)NH—C$_2$-C$_{12}$-alkenyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—C$_1$-C$_{12}$-alkyl, —NHC(NH)NH—C$_2$-C$_{12}$-alkenyl, —NHC(NH)NH—C$_2$-C$_{12}$-alkenyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, NHC(NH)—C$_1$-C$_{12}$-alkyl, —NHC(NH)—C$_2$-C$_{12}$-alkenyl, —NHC(NH)—C$_2$-C$_{12}$-alkenyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkenyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

The terms "C$_2$-C$_{12}$ alkynyl" or "C$_2$-C$_6$ alkynyl," as used herein, denote a monovalent group derived from a hydrocarbon moiety containing from two to twelve or two to six carbon atoms having at least one carbon-carbon triple bond by the removal of a single hydrogen atom. Representative alkynyl groups include, but are not limited to, for example, ethynyl, 1-propynyl, 1-butynyl, and the like.

The term "substituted alkynyl," as used herein, refers to a "C$_2$-C$_{12}$ alkynyl" or "C$_2$-C$_6$ alkynyl" group as previously defined, substituted by independent replacement or one, two, or three of the hydrogen atoms thereon with substituents including, but not limited to, —F, —Cl, —Br, —I, —OH, protected hydroxy, —NO$_2$, —CN, —C$_1$-C$_{12}$-alkyl optionally substituted with halogen, C$_2$-C$_{12}$-alkenyl optionally substituted with halogen, —C$_2$-C$_{12}$-alkynyl optionally substituted with halogen, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkenyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkenyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkenyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkenyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkenyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkenyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkenyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$-C$_{12}$-alkyl, —NHC(O)NH—C$_2$-C$_{12}$-alkenyl, —NHC(O)NH—C$_2$-C$_{12}$-alkenyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, NHC(S)NH—C$_1$-C$_{12}$-alkyl, —NHC(S)NH—C$_2$-C$_{12}$-alkenyl, —NHC(S)NH—C$_2$-C$_{12}$-alkenyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—C$_1$-C$_{12}$-alkyl, —NHC(NH)NH—C$_2$-C$_{12}$-alkenyl, —NHC(NH)NH—C$_2$-C$_{12}$-alkenyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, NHC(NH)—C$_1$-C$_{12}$-alkyl, —NHC(NH)—C$_2$-C$_{12}$-alkenyl, —NHC(NH)—C$_2$-C$_{12}$-alkenyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkenyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

The term "C$_1$-C$_6$ alkoxy," as used herein, refers to a C$_1$-C$_6$ alkyl group, as previously defined, attached to the parent molecular moiety through an oxygen atom. Examples of C$_1$-C$_6$-alkoxy include, but are not limited to, methoxy, ethoxy, propoxy, isopropoxy, n-butoxy, tert-butoxy, neopentoxy and n-hexoxy.

The terms "halo" and "halogen," as used herein, refer to an atom selected from fluorine, chlorine, bromine and iodine.

The term "aryl," as used herein, refers to a mono- or bicyclic carbocyclic ring system having one or two aromatic rings including, but not limited to, phenyl, naphthyl, tetrahydronaphthyl, indanyl, idenyl and the like.

The term "substituted aryl," as used herein, refers to an aryl group, as previously defined, substituted by independent replacement or one, two, or three of the hydrogen atoms thereon with substituents including, but not limited to, —F, —Cl, —Br, —I, —OH, protected hydroxy, —NO$_2$, —CN, —C$_1$-C$_{12}$-alkyl optionally substituted with halogen, C$_2$-C$_{12}$-alkenyl optionally substituted with halogen, —C$_2$-C$_{12}$-alkynyl optionally substituted with halogen, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkenyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkenyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkenyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkenyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkenyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkenyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkenyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$-C$_{12}$-alkyl, —NHC(O)NH—C$_2$-C$_{12}$-alkenyl, —NHC(O)NH—C$_2$-C$_{12}$-alkenyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, NHC(S)NH—C$_1$-C$_{12}$-alkyl, —NHC(S)NH—C$_2$-C$_{12}$-alkenyl, —NHC(S)NH—C$_2$-C$_{12}$-alkenyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—C$_1$-C$_{12}$-alkyl, —NHC(NH)NH—C$_2$-C$_{12}$-alkenyl, —NHC(NH)NH—C$_2$-C$_{12}$-alkenyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, NHC(NH)—C$_1$-C$_{12}$-alkyl, —NHC(NH)—C$_2$-C$_{12}$-alkenyl, —NHC(NH)—C$_2$-C$_{12}$-alkenyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkenyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

The term "arylalkyl," as used herein, refers to a C$_1$-C$_3$ alkyl or C$_1$-C$_6$ alkyl residue attached to an aryl ring. Examples include, but are not limited to, benzyl, phenethyl and the like.

The term "substituted arylalkyl," as used herein, refers to an arylalkyl group, as previously defined, substituted by independent replacement or one, two, or three of the hydrogen atoms thereon with substituents including, but not limited to, but not limited to, —F, —Cl, —Br, —I, —OH, protected hydroxy, —NO$_2$, —CN, —C$_1$-C$_{12}$-alkyl optionally substituted with halogen, C$_2$-C$_{12}$-alkenyl optionally substituted with halogen, —C$_2$-C$_{12}$-alkynyl optionally substituted with halogen, —NH$_2$, protected amino, —NH—C$_1$-C$_{12}$-alkyl, —NH—C$_2$-C$_{12}$-alkenyl, —NH—C$_2$-C$_{12}$-alkenyl, —NH—

$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, -O—$C_2$-$C_{12}$-alkenyl, —O—$C_2$-$C_{12}$-alkenyl, —O—$C_3$-$C_{12}$-cycloalkyl, —O-aryl, —O-heteroaryl, -O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —OCO$_2$—$C_3$-$C_{12}$-alkyl, —OCO$_2$—$C_2$-$C_{12}$-alkenyl, —OCO$_2$—$C_2$-$C_{12}$-alkenyl, —OCO$_2$—$C_3$-$C_{12}$-cycloalkyl, —OCO$_2$-aryl, —OCO$_2$-heteroaryl, —OCO$_2$-heterocycloalkyl, —OCONH$_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —NHCO$_2$—$C_1$-$C_{12}$-alkyl, —NHCO$_2$—$C_2$-$C_{12}$-alkenyl, —NHCO$_2$—$C_2$-$C_{12}$-alkenyl, —NHCO$_2$—$C_3$-$C_{12}$-cycloalkyl, —NHCO$_2$-aryl, —NHCO$_2$-heteroaryl, —NHCO$_2$-heterocycloalkyl, —NHC(O)NH$_2$, NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)NH$_2$, NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl —SO$_2$NH$_2$, —SO$_2$NH—$C_1$-$C_{12}$-alkyl, —SO$_2$NH—$C_2$-$C_{12}$-alkenyl, —SO$_2$NH—$C_2$-$C_{12}$-alkenyl, —SO$_2$NH—$C_3$-$C_{12}$-cycloalkyl, —SO$_2$NH-aryl, —SO$_2$NH-heteroaryl, —SO$_2$NH-heterocycloalkyl, —NHSO$_2$—$C_1$-$C_{12}$-alkyl, —NHSO$_2$—$C_2$-$C_{12}$-alkenyl, —NHSO$_2$—$C_2$-$C_{12}$-alkenyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$-$C_{12}$-cycloalkyl, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl.

The term "heteroaryl," as used herein, refers to a mono-, bi-, or tri-cyclic aromatic radical or ring having from five to ten ring atoms of which one ring atom is selected from S, O and N; zero, one or two ring atoms are additional heteroatoms independently selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "substituted heteroaryl," as used herein, refers to a heteroaryl group as previously defined, substituted by independent replacement or one, two, or three of the hydrogen atoms thereon with substituents including, but not limited to, —F, —Cl, —Br, —I, —OH, protected hydroxy, —NO$_2$, —CN, —$C_1$-$C_{12}$-alkyl optionally substituted with halogen, $C_2$-$C_{12}$-alkenyl optionally substituted with halogen, —$C_2$-$C_{12}$-alkynyl optionally substituted with halogen, —NH$_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_{12}$-alkenyl, —OCO$_2$—$C_2$-$C_{12}$-alkenyl, —OCO$_2$—$C_3$-$C_{12}$-cycloalkyl, —OCO$_2$-aryl, —OCO$_2$-heteroaryl, —OCO$_2$-heterocycloalkyl, —OCONH$_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —NHCO$_2$—$C_1$-$C_{12}$-alkyl, —NHCO$_2$—$C_2$-$C_{12}$-alkenyl, —NHCO$_2$—$C_2$-$C_{12}$-alkenyl, —NHCO$_2$—$C_3$-$C_{12}$-cycloalkyl, —NHCO$_2$-aryl, —NHCO$_2$-heteroaryl, —NHCO$_2$-heterocycloalkyl, —NHC(O)NH$_2$, NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)NH$_2$, NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl —SO$_2$NH$_2$, —SO$_2$NH—$C_1$-$C_{12}$-alkyl, —SO$_2$NH—$C_2$-$C_{12}$-alkenyl, —SO$_2$NH—$C_2$-$C_{12}$-alkenyl, —SO$_2$NH—$C_3$-$C_{12}$-cycloalkyl, —SO$_2$NH-aryl, —SO$_2$NH-heteroaryl, —SO$_2$NH-heterocycloalkyl, —NHSO$_2$—$C_1$-$C_{12}$-alkyl, —NHSO$_2$—$C_2$-$C_{12}$-alkenyl, NHSO$_2$—$C_2$-$C_{12}$-alkenyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

The term "C$_3$-C$_{12}$-cycloalkyl," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo [2.2.1]heptyl, and bicyclo [2.2.2] octyl.

The term "substituted C$_3$-C$_{12}$-cycloalkyl," as used herein, refers to a C$_3$-C$_{12}$-cycloalkyl group as previously defined, substituted by independent replacement or one, two, or three of the hydrogen atoms thereon with substituents including, but not limited to, —F, —Cl, —Br, —I, —OH, protected hydroxy, —NO$_2$, —CN, —C$_1$-C$_{12}$-alkyl optionally substituted with halogen, C$_2$-C$_{12}$-alkenyl optionally substituted with halogen, —C$_2$-C$_{12}$-alkynyl optionally substituted with halogen, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkenyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkenyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkenyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkenyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkenyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkenyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkenyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$-C$_{12}$-alkyl, —NHC(O)NH—C$_2$-C$_{12}$-alkenyl, —NHC(O)NH—C$_2$-C$_{12}$-alkenyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, NHC(S)NH—C$_1$-C$_{12}$-alkyl, —NHC(S)NH—C$_2$-C$_{12}$-alkenyl, —NHC(S)NH—C$_2$-C$_{12}$-alkenyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—C$_1$-C$_{12}$-alkyl, —NHC(NH)NH—C$_2$-C$_{12}$-alkenyl, —NHC(NH)NH—C$_2$-C$_{12}$-alkenyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, NHC(NH)—C$_1$-C$_{12}$-alkyl, —NHC(NH)—C$_2$-C$_{12}$-alkenyl, —NHC(NH)—C$_2$-C$_{12}$-alkenyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkenyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

The term "heterocycloalkyl," as used herein, refers to a non-aromatic 5-, 6- or 7-membered hydrocarbon ring or a bi- or tri-cyclic group fused hydrocarbon system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "substituted heterocycloalkyl," as used herein, refers to a heterocycloalkyl group, as previously defined, substituted by independent replacement or one, two, or three of the hydrogen atoms thereon with substituents including, but not limited to, —F, —Cl, —Br, —I, —OH, protected hydroxy, —NO$_2$, —CN, —C$_1$-C$_{12}$-alkyl optionally substituted with halogen, C$_2$-C$_{12}$-alkenyl optionally substituted with halogen, —C$_2$-C$_{12}$-alkynyl optionally substituted with halogen, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, -O—C$_2$-C$_{12}$-alkenyl, —O—C$_2$-C$_{12}$-alkenyl, —O—C$_3$-C$_{12}$-cycloalkyl, —O-aryl, —O-heteroaryl, -O-heterocycloalkyl, —C(O)—C$_1$-C$_{12}$-alkyl, —C(O)—C$_2$-C$_{12}$-alkenyl, —C(O)—C$_2$-C$_{12}$-alkenyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkenyl, —CONH—C$_3$-C$_{12}$-cycloalkyl, —CONH-aryl, —CONH-heteroaryl, —CONH-heterocycloalkyl, —OCO$_2$—C$_3$-C$_{12}$-alkyl, —OCO$_2$—C$_2$-C$_{12}$-alkenyl, —OCO$_2$—C$_2$-C$_{12}$-alkenyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkenyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkenyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkenyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$-C$_{12}$-alkyl, —NHC(O)NH—C$_2$-C$_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)NH$_2$, NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl —SO$_2$NH$_2$, —SO$_2$NH—$C_1$-$C_{12}$-alkyl, —SO$_2$NH—$C_2$-$C_{12}$-alkenyl, —SO$_2$NH—$C_2$-$C_{12}$-alkenyl, —SO$_2$NH—$C_3$-$C_{12}$-cycloalkyl, —SO$_2$NH-aryl, —SO$_2$NH-heteroaryl, —SO$_2$NH-heterocycloalkyl, —NHSO$_2$—$C_1$-$C_{12}$-alkyl, —NHSO$_2$—$C_2$-$C_{12}$-alkenyl, —NHSO$_2$—$C_2$-$C_{12}$-alkenyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$-$C_{12}$-cycloalkyl, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl.

The term "heteroarylalkyl," as used herein, refers to a $C_1$-$C_3$ alkyl or $C_1$-$C_6$ alkyl residue attached to a heteroaryl ring. Examples include, but are not limited to, pyridinylmethyl, pyrimidinylethyl and the like.

The term "substituted heteroarylalkyl," as used herein, refers to a heteroarylalkyl group, as previously defined, substituted by independent replacement or one, two, or three of the hydrogen atoms thereon with substituents including, but not limited to, —F, —Cl, —Br, —I, —OH, protected hydroxy, —NO$_2$, —CN, —$C_1$-$C_{12}$-alkyl optionally substituted with halogen, —$C_2$-$C_{12}$-alkenyl optionally substituted with halogen, —$C_2$-$C_{12}$-alkynyl optionally substituted with halogen, —NH$_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_{12}$-alkenyl, —OCO$_2$—$C_2$-$C_{12}$-alkenyl, —OCO$_2$—$C_3$-$C_{12}$-cycloalkyl, —OCO$_2$-aryl, —OCO$_2$-heteroaryl, —OCO$_2$-heterocycloalkyl, —OCONH$_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —NHCO$_2$—$C_1$-$C_{12}$-alkyl, —NHCO$_2$—$C_2$-$C_{12}$-alkenyl, —NHCO$_2$—$C_2$-$C_{12}$-alkenyl, —NHCO$_2$—$C_3$-$C_{12}$-cycloalkyl, —NHCO$_2$-aryl, —NHCO$_2$-heteroaryl, —NHCO$_2$-heterocycloalkyl, —NHC(O)NH$_2$, NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)NH$_2$, NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl —SO$_2$NH$_2$, —SO$_2$NH—$C_1$-$C_{12}$-alkyl, —SO$_2$NH—$C_2$-$C_{12}$-alkenyl, —SO$_2$NH—$C_2$-$C_{12}$-alkenyl, —SO$_2$NH—$C_3$-$C_{12}$-cycloalkyl, —SO$_2$NH-aryl, —SO$_2$NH-heteroaryl, —SO$_2$NH-heterocycloalkyl, —NHSO$_2$—$C_1$-$C_{12}$-alkyl, —NHSO$_2$—$C_2$-$C_{12}$-alkenyl, NHSO$_2$—$C_2$-$C_{12}$-alkenyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$-$C_{12}$-cycloalkyl, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl.

The term "$C_1$-$C_3$-alkyl-amino," as used herein, refers to one or two $C_1$-$C_3$-alkyl groups, as previously defined, attached to the parent molecular moiety through a nitrogen atom. Examples of $C_1$-$C_3$-alkyl-amino include, but are not limited to, methylamino, dimethylamino, ethylamino, diethylamino, and propylamino.

The term "alkylamino" refers to a group having the structure —NH($C_1$-$C_{12}$ alkyl) where $C_1$-$C_{12}$ alkyl is as previously defined.

The term "dialkylamino" refers to a group having the structure —N($C_1$-$C_{12}$ alkyl) ($C_1$-$C_{12}$ alkyl), where $C_1$-$C_{12}$ alkyl is as previously defined. Examples of dialkylamino are, but not limited to, dimethylamino, diethylamino, methylethylamino, piperidino, and the like.

The term "alkoxycarbonyl" represents an ester group, i.e., an alkoxy group, attached to the parent molecular moiety through a carbonyl group such as methoxycarbonyl, ethoxycarbonyl, and the like.

The term "carboxaldehyde," as used herein, refers to a group of formula —CHO.

The term "carboxy," as used herein, refers to a group of formula —COOH.

The term "carboxamide," as used herein, refers to a group of formula —C(O)NH($C_1$-$C_{12}$ alkyl) or —C(O)N($C_1$-$C_{12}$ alkyl) ($C_1$-$C_{12}$ alkyl), —C(O)NH$_2$, and the like.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, *Protective Groups in Organic Synthesis,* 3rd edition, John Wiley & Sons, New York (1999). Examples of hydroxy protecting groups include, but are not limited to, methylthiomethyl, tert-butyl-dimethylsilyl, tert-butyldiphenylsilyl, acyl substituted with an aromatic group and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al, Vol. II, in the *Techniques of Chemistry Series,* John Wiley & Sons, NY, 1986.

The term "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

"An effective amount," as used herein, refers to an amount of a compound which confers a therapeutic effect on the treated subject. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the compounds of this invention, including the compounds of formulae described herein, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

Pharmaceutical Compositions

The pharmaceutical compositions of the present invention comprise a therapeutically effective amount of a compound or compounds of the present invention (e.g. those of the formulae delineated herein) formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol.

Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, immune disorders are treated or prevented in a patient such as a human or other animals by administering to the patient a therapeutically effective amount of a compound of the invention, in such amounts and for such time as is necessary to achieve the desired result.

By a "therapeutically effective amount" of a compound of the invention is meant a sufficient amount of the compound to treat the immune disorders delineated herein, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Immunosuppression Activity

Calcineurin Inhibition Assay

The immunosuppressive activity of cyclosporin is mediated through inhibition of the phosphatase activity of the enzyme calcineurin by a cyclophilin-cyclosporin complex. Thus, calcineurin inhibition is widely used as an in vitro measure of the activity of cyclosporin analogs.

Compounds were tested in an assay based on the Biomol Green Calcineurin Assay Kit supplied by Biomol (Plymouth Meeting, Pa.), supplemented with cyclophilin A for enzyme inhibition. The activity of the recombinant human calcineurin was determined by release of phosphate from a phosphopeptide representing a fragment of camp-dependent protein kinase. Phosphate release was determined using the calorimetric detection reagent Biomol Green.

Compounds in dimethyl sulfoxide (DMSO) (2.4 µl) were added to a 96-well microplate and mixed with 50 µl assay buffer (50 mM Tris, pH 7.5, 0.1 M sodium chloride, 6 mM magnesium chloride, 0.5 mM dithiothreitol, 0.025% NP-40, 0.5 mM calcium chloride, 0.25 µM calmodulin) containing 5 µM cyclophilin and 20 units of calcineurin. After warming to 37° C. for 15 min, the enzymatic reaction was initiated by addition of phosphopeptide (7.5 µl) to give a final concentration of 94 µM. Phosphate release after 60 min at 37° C. was determined by addition of Biomol Green (100 µl) and measurement of the absorbance at 620 nm after 15 min at room temperature.

$IC_{50}$ values were calculated from determinations of enzyme activity at inhibitor concentrations ranging from 20 to 0.006 µM.

Murine Mixed Lymphocyte Reaction

Approximately $0.5 \times 10^6$ lymphocytes from the spleen of female (8-10 weeks) Balb/c mice are incubated for 5 days in 0.2 ml cell growth medium with ca. $0.5 \times 10^6$ lymphocytes from the spleen of female (8-10 weeks) albino brown agouti (CBA) mice. Test substance is added to the medium at various concentrations. Activity is assessed by ability to suppress proliferation-associated DNA synthesis as determined by incorporation of radiolabelled thymidine.

Mishell-Dutton Test

Approximately $10^7$ lymphocytes from the spleen of CF 1, female mice are co-cultured with ca. $3 \times 10^7$ sheep erythrocytes for 3 days. Test substance is added to the incubation medium in varying concentrations. Lymphocytes are harvested and plated onto agar with fresh sheep erythrocytes as antigen. Sensitized lymphocytes secrete antibody that coats the erythrocytes, which lyse to form a plaque in the presence of complement. Activity is assessed by reduction in the number of plaque forming, i.e., antibody product, cells.

Influence on Allergen-Induced Pulmonary Eosinophilia (in vitro)

Male Himalayan spotted guinea pigs (300 g, BRL) are sensitized to ovalbumin (OA) by i.p. injection of 1 ml of a suspension of OA (10 µg/ml) with $Al(OH)_3$ (100 mg) and B-pertussis vaccine (0.25 ml) in saline (0.9% w/v). For oral studies the procedure is repeated 1× after 2 weeks and the animals are used one week later. For inhalation studies the procedure is repeated 2× at 3-week intervals and the animals are used one week after the last injection.

Challenge is affected employing a saline solution of OA, nebulized for discharge into an exposure chamber. Test animals are exposed to OA by nose-only inhalation for 60 minutes. For inhalation studies, OA solution is used at a concentration of 0.01%.

Test substance is administered by inhalation and/or orally. For oral studies, test substance is administered p.o. in olive oil 1× daily for 3 days or in powder form in methylcellulose once prior to OA challenge. On day 3, test animals receive test substance 1.5 hours prior to and 6 hours after OA challenge. For inhalation studies, test substance is micronised for delivery to test animals restrained within a flow-past, nose-only inhalation chamber. Administration by inhalation is effected 15 minutes prior to OA challenge.

Efficacy of administered test substance is determined by bronchoalveolar lavage (BAL) and cell counting. For this purpose animals are sacrificed with Na pento-barbitone (100 mg/kg i.p.) and the trachea is exposed and cannulated. 5 successive 10 ml aliqots of $Ca^{2+}$ and $Mg^{2+}$ free Hank's balanced salt solution (HBSS), containing bovine serum albumin (BSA, 0.3%), EDTA (10 mM) and 4-(2-hydroxyethyl)-1-piperazineethanesulfonic acid (HEPES) (10 mM) is then introduced into the lung and immediately aspirated by gentle compression of the lung tissue. Total cell counts in pooled eluates are determined using an automatic cell counter. Lavage fluid is centrifuged at 200 g for 10 minutes and the cell pellet resuspended in 1 ml of supplemented HBSS. 10 µl of this cell suspension is added to 190 µl of Turk's solution (1:20) dilution). Differential cell counts are made from smears stained by Diff-Quick. Cells are identified and counted under oil immersion (×1,000). A minimum of 500 cells per smear are counted and the total population of each cell type is calculated.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which may be used in the descriptions of the scheme and the examples that follow are:

Ac for acetyl;
AIBN for azobisisobutyronitrile;
$Bu_3SnH$ for tributyltin hydride;
CDI for carbonyldiimidazole;
dba for dibenzylidene acetone;

dppb for diphenylphosphino butane;
DBU for 1,8-diazabicyclo[5.4.0]undec-7-ene;
DEAD for diethylazodicarboxylate;
DIBAL-H for diisopropyl aluminum hydride;
DMAP for dimethylaminopyridine;
DMF for dimethyl formamide;
DPPA for diphenylphosphoryl azide;
LAH for lithium aluminum hydride;
EtOAc for ethyl acetate;
MeOH for methanol;
NaN(TMS)$_2$ for sodium bis(trimethylsilyl)amide;
NMMO for N-methylmorpholine N-oxide;
TEA for triethylamine;
THF for tetrahydrofuran;
TPP or PPh$_3$ for triphenylphosphine;
MOM for methoxymethyl;
Boc for t-butoxycarbonyl;
Bz for benzyl;
Ph for phenyl;
POPd for dihydrogen dichlorobis(di-tert-butylphosphinito-κP)palladate(II);
Py for pyridine;
TBS for tert-butyl dimethylsilyl;
TMS for trimethylsilyl;
TES for trimethylsilyl;
Sar for Sarcosine;
MeLeu for N-Methyl-Leucine;
Val for Valine;
Ala for Alanine;
MeVal for N-Methyl Valine;
Et for Ethyl;
Ph for Phenyl; and
MeBmt for N-Methyl-butenyl-threonine.

Synthetic Methods

The compounds and processes of the present invention will be better understood in connection with the following synthetic schemes that illustrate the methods by which the compounds of the invention may be prepared.

The synthetic schemes contained herein refer to modifications to formula A of formula I, as previously defined.

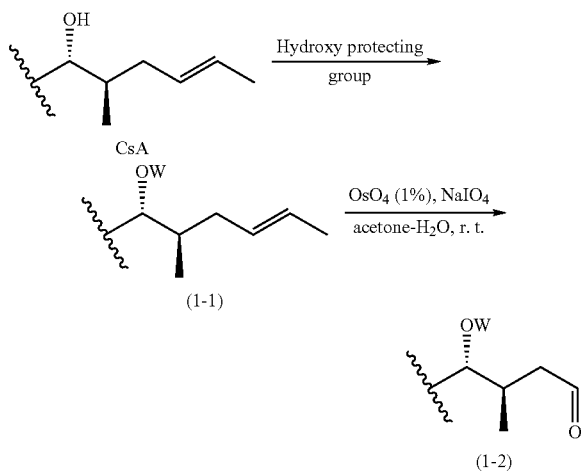

Cyclosporin A (CsA) can be converted to aldehyde (1-2) through first protecting the hydroxy of the MeBmt residue of CsA as an acetate ester to form a compound of formula (1-1). Other suitable hydroxy protecting groups include, but are not limited to, TMS, TES, TBS, or COCF$_3$ (for further details concerning these and other hydroxy protecting groups known in the art, as well as there incorporation and removal, please see T. W. Greene and P. G. M. Wuts, *Protective Groups in Organic Synthesis*, 2d. Ed., John Wiley and Sons (1991).) Aldehyde (1-2) can then be formed through creation of the corresponding diol by treatment with OsO$_4$ followed by the oxidative cleavage of the resulting diol with NaIO$_4$ (for further details of diol formation with OSO$_4$, please see Akashi, K, Palermo, R. E., Sharpless, K. B., *J. Org. Chem.* 1978, 43, 2003-06; and for further details concerning the oxidative cleavage of diols with NaIO$_4$, please see Zhong, Y. L., Shing, T. K. M., *J. Org. Chem.* 1997, 62, 2622-24). This reaction may also be performed through ozonolysis (see Park, S. B., Meier, G. P. *Tetrahedron Lett.* 1989, 30, 4215-4218).

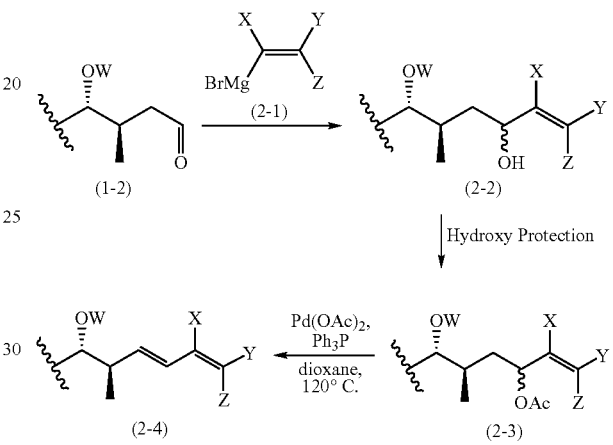

Compound of formula (1-2) may be treated with vinyl Grignard reagent of formula (2-1), where X, Y, and Z are as previously defined, to form the allyl alcohol (2-2), where W, X, Y, and Z are as previously defined. The requisite Grignard reagents are readily available via the reaction of a variety of vinyl halides with magnesium under standard conditions (for further details, please see B. S. Furniss, A. J. Hannaford, P. W. G. Smith, A. R. Tatchell "Vogel's Textbook of Practical Organic Chemistry" 5$^{th}$ ed., Longman, 1989 or G. S. Silverman, P. E. Rakita in *Kirk-Othmer Encyclopedia of Chemical Technology* vol. 12 (Wiley-Interscience, New York, 4th ed., 1994) pp 768-786). The addition is performed in an inert solvent, generally at low temperature. Suitable solvents include, but are not limited to tetrahydrofuran, diethylether, 1,4-dioxane, 1,2-dimethoxyethane, and hexanes. Preferably the solvent is tetrahydrofuran or diethylether. Preferably the reaction is run at −78° to 0° C.

Allyl alcohol of formula (2-2) is then protected with a hydroxy protecting group to form a compound of formula (2-3). Suitable hydroxy protecting groups include, but are not limited to, acetate and methyl carbamate (for further details on suitable hydroxy protecting groups see T. W. Greene and P. G. M. Wuts, *Protective Groups in Organic Synthesis*, 2d. Ed., John Wiley and Sons (1991)). The protected allylic alcohol then undergoes a palladium-catalyzed elimination to form conjugated diene compound of formula (2-4) (for further details, please see Tsuji, J. et al, *Tetrahedron Lett.* 1978, 24, 2075-2078). Suitable solvents include, but are not limited to, dioxane, toluene, or t-butyl alcohol. A suitable palladium catalyst is palladium acetate in the presence of triphenylphosphine or (PPh$_3$)$_4$Pd. Suitable reaction conditions are at a temperature up to reflux for a duration of at least one hour.

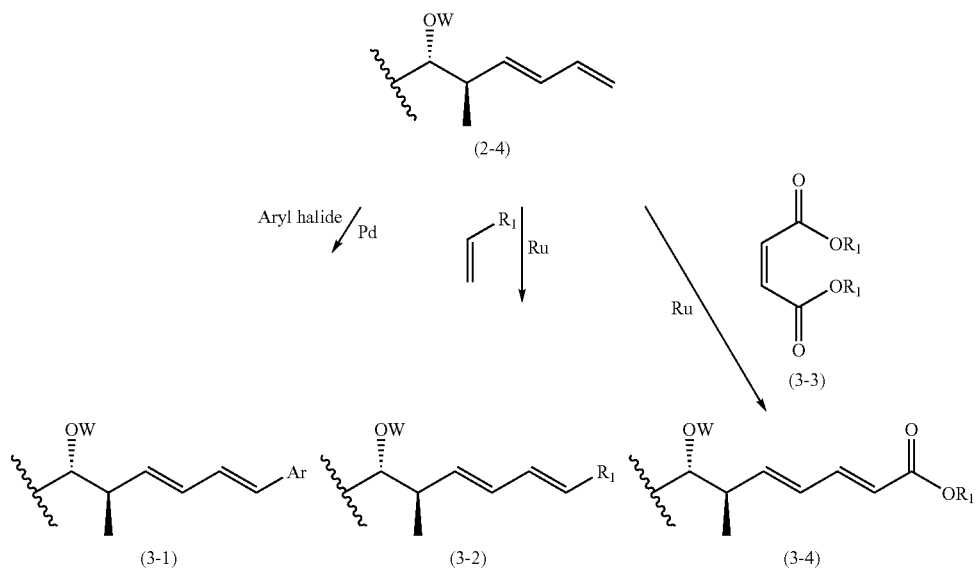

Compounds of the invention according to formula (2-4) are also capable of further functionalization to generate compounds of the present invention. Alkene (2-4) can be treated with an aryl halide or aryl triflate in the presence of a palladium catalyst [Pd(0) or Pd(II)] to provide compound (3-1): (See (a) Heck, Palladium Reagents in Organic Synthesis, Academic Press: New York, 1985, Chapter 1; (b) Sonogashira, Comprehensive Organic Synthesis, Volume 3, Chapters 2,4; (c) Sonogashira, *Synthesis* 1977, 777.). Under the Heck coupling conditions, regioisomers and stereoisomers of the double bond are possible. Alternatively, compound (2-4) can undergo a cross metathesis reaction with vinyl derivatives using ruthenium catalysts to give compounds of formula (3-2), where $R_1$ is as previously defined (see (a) *J. Org. Chem.* 2000, 65, 2204-2207; (b) Reviews: *Synlett.* 1999, 2, 267; (c) Reviews: Ivin, K. J.; Mol, J. C. *Olefin Metathesis and Metathesis Polymerization*, $2^{nd}$ ed.; Academic Press: New York, 1997; (d) *J. Org. Chem.* 1999, 64, 4798-4816; (e) *Angew. Chem., Int. Ed. Engl.* 1997, 36, 2036-2056; (f) *Tetrahedron* 1998, 54, 4413-4450; (e) Connon, S. J. and Blechert, S. *Angew. Chem. Int. Ed.* 2003, 42, 1900-23). In addition, compound of formula (2-4) may be subjected to cross metathesis reaction conditions in the presence of compounds of formula (3-3), where $R_1$ is as previously defined, to yield conjugated esters of formula (3-4).

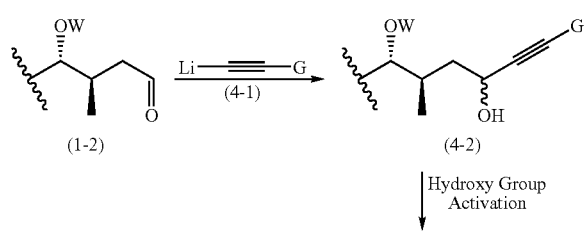

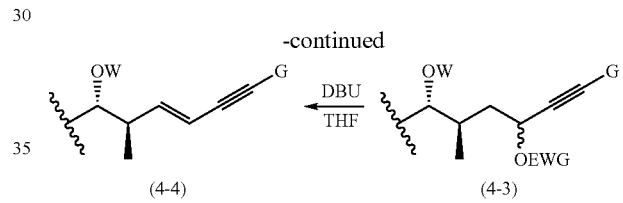

Compound of formula (1-2) may be treated with lithium acetylide of formula (4-1), where G is as previously defined, to form the propargyl alcohol (4-2). The requisite lithium reagents are readily available via the reaction of a variety of acetylenes with n-butyl lithium under standard conditions (for further details, please see B. S. Furniss, A. J. Hannaford, P. W. G. Smith, A. R. Tatchell "Vogel's Textbook of Practical Organic Chemistry" 5th ed., Longman, 1989 or G. S. Silverman, P. E. Rakita in *Kirk-Othmer Encyclopedia of Chemical Technology* vol. 12 (Wiley-Interscience, New York, 4th ed., 1994)). The reaction can be performed in an inert solvent, generally at low temperature. Suitable solvents include, but are not limited to tetrahydrofuran, diethylether, 1,4-dioxane, 1,2-dimethoxyethane, and hexanes. Preferably the solvent is tetrahydrofuran or diethylether. Preferably the reaction is run at −78°.

Propargyl alcohol of formula (4-2) is then activated with a an electron-withdrawing group (EWG) to form a compound of formula (4-3). Suitable hydroxy activating groups include, but are not limited to, mesylate and triflate. The activated propargyl alcohol then undergoes elimination to form conjugated ene-yne compound of formula (4-4) (for further details, please see Tsuji, J. et al, *Tetrahedron Lett.* 1978, 24, 2075-2078). Suitable solvents include, but are not limited to, toluene or THF. Suitable reaction conditions are at a temperature up to reflux.

Scheme 5

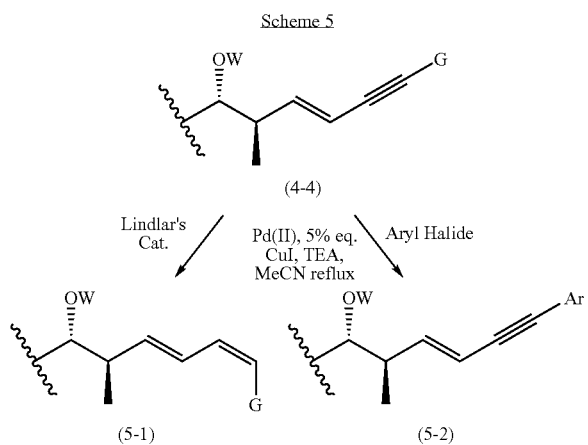

Compound of formula (4-4), where G is as previously defined, can undergo catalytic hydrogenation via Lindlar's catalyst to yield the cis conjugated diene of formula (5-1) (for further details, please see H. Lindlar and R. Dubois, *Org. Synth.* V, 880 (1973)). In addition, compound of formula (4-4), when G=H, may be treated with aryl halides under Sonagashira conditions to afford compounds of formula (5-2) (for further details of the Sonogashira reaction see Sonogashira, *Comprehensive Organic Synthesis*, Volume 3, Chapters 2,4 and Sonogashira, *Synthesis* 1977, 777).

EXAMPLES

The procedures described above for preparing the compounds of the present invention will be better understood in connection with the following examples, which are intended to be illustrative only and not limiting of the scope of the invention. Various changes and modifications of the disclosed embodiments will be apparent to those skilled in the art. Such changes and modifications, including without limitation, those relating to the chemical structures, substituents, derivatives, intermediates, syntheses, formulations and/or methods for the invention may be made without departing from the spirit of the invention and the scope of the appended claims.

Example 1

A Compound of Formula I, wherein a is of the Formula (1-2) and W is Ac

Step a. A Compound of Formula I, wherein A is of the Formula (1-1) and W is Ac.

To a solution of cyclosporine A (105 g, 87.42 mmol), DMAP (1.0 g, 8.18 mmol, 9.4% eq), Py (16 ml, 197.8 mmol, 2.26 eq ) in $CH_2Cl_2$ (100 ml) at 0° C. is added $Ac_2O$ (30 ml, 317.65 mmol, 3.63 eq). The mixture is stirred from 0° C. to room temperature over night. After the reaction is complete as judged by mass spectrometry analysis, solvent ($CH_2Cl_2$) is removed under vacuum. The white solid residue is dissolved in ethyl acetate, washed with water (300 ml), 1.0 HCl (2×200 ml), water (200 ml), sat. $NaHCO_3$ (200 ml), brine (200 ml), dried with $Na_2SO_4$, filtered and evaporated. The residue is lyophilized to give a white solid. m/e⁺ for $C_{64}H_{113}N_{11}O_{13}$ 1243.85, found 1244.51 (m+H)⁺, 1266.52 (m+Na)⁺

Step b. A Compound of Formula I, wherein A is of the Formula (1-2) and W is Ac.

To a solution of cyclosporine A acetate from Step a (40.2 g, 32.32 mmol) in acetone (300 ml)-$H_2O$ (100 ml) at room temperature is added $OsO_4$ (58 mg, 0.228 mmol, 0.7% eq). The solution becomes black immediately. Then $NaIO_4$ (34.7 g, 162.23 mmol, 5.0 eq) is added. The black color fads and white solid precipitates out upon stirring. The reaction is monitored by TLC and mass spectrometry analysis. Upon the completion of the reaction, the mixture is concentrated under vacuum in a hood to remove most of the acetone. The residue is extracted with ethyl acetate. The organic solution is washed with water (1×200 ml), aqueous sodium sulfite solution until the aqueous layer is colorless (yellow color indicated the presence of oxidizing agent such $NaIO_4$), sat. $NaHCO_3$ (to remove acid by-product), water again and finally washed with brine. After drying with $Na_2SO_4$, the solution is evaporated and lyophilized to give the title compound as a white solid. The crude product might be purified by silica gel chromatography (eluted with 50% ethyl acetate-hexane, then 100% ethyl acetate). m/e⁺ for $C_{62}H_{109}N_{11}O_{14}$ 1231.82, found 1232.22 (m+H)⁺, 1249.26, (m+$NH_4$)⁺, 1254.19 (m+Na)⁺.

Example 2

A Compound of Formula I, wherein Q is

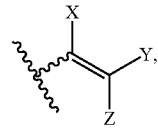

W is Ac and X=Y=Z=hydrogen

Step a. A Compound of Formula I: A is Formula (2-2) wherein X=Y=Z=hydrogen.

A solution of vinylmagnesium bromide (40 ml, 0.5 M in THF, 20 mmol) is diluted with 50 ml THF and cooled to –78° C. Then a solution of the title compound from Example 1 (4.3 g, 3.49 mmol) in THF (2 ml) is added dropwise. After addition, the mixture is stirred for 20-30 min and quenched with aq. $NH_4Cl$ at –78° C. After warm up to room temperature, the mixture is extracted with ethyl acetate (2×100 ml). The combined organic solution is washed with brine, dried with $Na_2SO_4$, concentrated and dried by lyophilization to afford a light yellow solid (4.66 g). m/e⁺ for $C_{64}H_{113}N_{11}O_{14}$ 1259.85, found 1282.90 (m+Na)⁺.

Step b. A Compound of Formula I: A is Formula (2-3) wherein X=Y=Z=hydrogen

To a solution of cyclosporine A allyl alcohol of Step a (4.66 g, 3.77 mmol), DMAP (45 mg, 0.36 mmol, 9.5% eq), Py (0.72 ml, 8.90 mmol, 2.36 eq) in $CH_2Cl_2$ (5.0 ml) is added $Ac_2O$ (1.0 ml). The mixture is stirred at room until the reaction is complete as judged by mass spectrometry analysis (about 3 hrs). Then, the mixture is diluted with ethyl acetate (50 ml), washed with water (1×30 ml), 1.0 HCl (2×20 ml), water (1×20 ml), sat. $NaHCO_3$ (1×20 ml) and brine (1×20 ml), dried with $Na_2SO_4$, filtered and evaporated. The crude product is purified by silica gel chromatography (eluted with 50% ethyl acetate-hexane, then 100% ethyl acetate) to give diacetate as a white solid. m/e⁺ for $C_{66}H_{115}N_{11}O_{15}$ 1301.86, found 1302.78 (m+H)⁺, 1319.81 (m+$NH_4$)⁺, 1324.77 (m+Na)⁺.

Step c. A Compound of Formula I wherein Q is

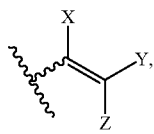

W is Ac and X=Y=Z=hydrogen.

A mixture of diacetate (2.0 g, 1.54 mmol), Ph$_3$P (183 mg, 0.70 mmol), Pd(OAc)$_2$ (73.8 mg, 0.32 mmol) in dioxane (10 ml) is degassed twice and heated at 120° C. The solution becomes black in about 30 min and the reaction is complete in 1 hr as judged by mass spectrometry analysis. Solvent is evaporated and the crude product is purified by silica gel chromatography (eluted with 50% ethyl acetate-hexane, then 100% ethyl acetate) to give the title compound product as a light yellow solid. m/e$^+$ for C$_{64}$H$_{111}$N$_{11}$O$_{13}$ 1241.84, found 1242.97 (m+H)$^+$, 1260.00 (m+NH$_4$)$^+$, 1264.96 (m+Na)$^+$.

Example 3

A Compound of Formula I, wherein Q is

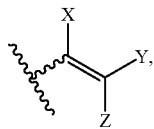

W is H and X=Y=Z=hydrogen

A solution of diene acetate of Example 2 (100 mg, 0.080 mmol), K$_2$CO$_3$ (55 mg, 0.40 mmol) in MeOH (2 ml) is heated to 50° C. for 2-3 hr. After cooled to room temperature, the mixture is diluted with ethyl acetate (20 ml), washed with aq. NH$_4$Cl and brine, dried with Na$_2$SO$_4$ and concentrated. The crude product is purified by preparative TLC (eluted 100% ethyl acetate) to give the title compound as a white solid. m/e$^+$ for C$_{62}$H$_{109}$N$_{11}$O$_{12}$ 1199.82, found 1200.89 (m+H)$^+$, 1222.87 (m+Na)$^+$.

Example 4

A Compound of Formula I, wherein Q is

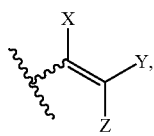

Y is CH$_3$, and W=X=Z=hydrogen

Step a. A Compound of Formula I, wherein A is of the Formula (2-2) Y is CH$_3$, and X=Z=hydrogen.

To a solution of cyclosporine aldehyde of Example 1 (995 mg, 0.80 mmol) in THF (3 ml) at −78° C. is added a solution of 1-propenylmagnesium bromide (18 ml, 0.5 M in THF). After addition, the mixture is stirred for 20-30 min and quenched with aq. NH$_4$Cl at −78° C. After warm up to room temperature, the mixture is diluted with ethyl acetate (50 ml), washed with sat. NH$_4$Cl (30 ml), brine (30 ml), dried with Na$_2$SO$_4$, concentrated and dried by lyophilization to afford a light yellow solid. m/e$^+$ for C$_{65}$H$_{115}$N$_{11}$O$_{14}$ 1273.86, found 1274.95 (m+H)$^+$, 1291.85 (m+NH$_4$)$^+$, 1296.85 (m+Na)$^+$.

Step b. A Compound of Formula I, wherein A is of the Formula (2-3) Y is CH$_3$, and X=Z=hydrogen.

To a solution of cyclosporine A allyl alcohol of Step a (90 mg, 0.071 mmol), DMAP (50 mg), and Py (0.50 ml) in CH$_2$Cl$_2$ (0.5 ml) at room is added Ac$_2$O (0.2 ml). The mixture is stirred at room until the reaction is complete as judged by mass spectrometry analysis (about 3 hrs). Then, the mixture is diluted with ethyl acetate (20 ml), washed with 1.0 HCl (10 ml), water (10 ml), sat. NaHCO$_3$ (10 ml) and brine (10 ml), dried with Na$_2$SO$_4$, filtered and evaporated. The crude product is purified by preparative TLC (eluted 100% ethyl acetate) to give the diacetate compound of Step c as a white solid. m/e$^+$ for C$_{67}$H$_{117}$N$_{11}$O$_{15}$ 1315.87, found 1316.87 (m+H)$^+$, 1333.90 (m+NH$_4$)$^+$, 1338.85 (m+Na)$^+$.

Step c. A Compound of Formula I, wherein Q is

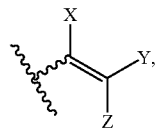

Y is CH$_3$, and W=X=Z=hydrogen.

A mixture of diacetate (240 mg, 0.182 mmol), Ph$_3$P (31 mg, 0.118 mmol), Pd(OAc)$_2$ (7.1 mg, 0.0316 mmol) in dioxane (2 ml) is degassed twice and heated at 120° C. The solution became black in about 30 min and the reaction is continued overnight. Mass spectrometry analysis indicated that the reaction is not complete. Solvent is evaporated and the product is separated from the starting material by preparative TLC (eluted with 100% ethyl acetate). The product (contained triphenylphosphene by-product) is dissolved in MeOH and stirred with K$_2$CO$_3$ (75 mg, 3 eq.) under 50° C. for 3 hrs. After removal of MeOH by evaporation, the residue is dissolved in ethyl acetate and filtered through a short silica gel pad. The filtrate is concentrated and the crude product is purified by preparative TLC (eluted with 100% ethyl acetate) to give the title compound. m/e$^+$ for C$_{63}$H$_{111}$N$_{11}$O$_{12}$ 1213.84, found 1214.84 (m+H)$^+$, 1236.84 (m+Na).

Example 5

A Compound of Formula I, wherein Q is

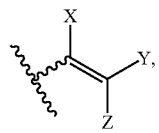

Y=Z=CH$_3$, and W=X=hydrogen

Step a. A Compound of Formula I, wherein A is of the Formula (2-2) Y=Z=CH$_3$, and X=hydrogen.

To a solution of cyclosporine adehyde of Example 1 (150 mg, 0.12 mmol) in THF (3 ml) at −78° C. is added a solution of 2-methyl-1-propenylmagnesium bromide (2.4 ml, 0.5 M in THF). After addition, the mixture is stirred for 20-30 min and quenched with aq. NH$_4$Cl at −78° C. After warm up to room temperature, the mixture is diluted with ethyl acetate (50 ml), washed with sat. NH$_4$Cl (30 ml), brine (30 ml), dried with Na$_2$SO$_4$, concentrated and dried by lyophilization to afford a light yellow solid. m/e$^+$ for C$_{66}$H$_{117}$N$_{11}$O$_{14}$ 1287.88, found 1288.87 (m+H)$^+$, 1310.87 (m+Na)$^+$.

Step b. A Compound of Formula I, wherein A is of the Formula (2-3) Y=Z=CH$_3$, and X=hydrogen.

To a solution of cyclosporine A allyl alcohol of Step a (90 mg, 0.071 mmol), DMAP (50 mg), and Py (0.50 ml) in CH$_2$Cl$_2$ (0.5 ml) at room is added Ac$_2$O (0.2 ml). The mixture is stirred at room until the reaction is complete as judged by mass spectrometry analysis (about 3 hrs). Then, the mixture is diluted with ethyl acetate (20 ml), washed with 1.0 HCl (10 ml), water (10 ml), sat. NaHCO$_3$ (10 ml) and brine (10 ml), dried with Na$_2$SO$_4$, filtered and evaporated. The crude product is purified by preparative TLC (eluted 100% ethyl acetate) to give the diacetate compound of Step c as a white solid. m/e$^+$ for C$_{68}$H$_{119}$N$_{11}$O$_{15}$ 1329.89, found 1330.66 (m+H)$^+$, 1347.68 (m+NH$_4$)$^+$, 1352.66 (m+Na)$^+$.

Step c. A Compound of Formula I, wherein Q is

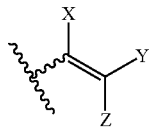

Y=Z=CH$_3$, and X=W=hydrogen.

A mixture of diacetate formed in Step b and Ph$_3$P (31 mg), Pd(OAc)$_2$ (12.71 mg, in dioxane (2 ml) is degassed twice and heated at 120° C. The solution became black in about 30 min and the reaction is continued overnight. Mass spectrometry analysis indicated that the reaction is not complete. Solvent is evaporated and the product is separated from the starting material by preparative TLC (eluted with 100% ethyl acetate). The product (contained triphenylphosphene by-product) is dissolved in MeOH and stirred with K$_2$CO$_3$ (75 mg, 3 eq.) under 50° C. for 3 hrs. After removal of MeOH by evaporation, the residue is dissolved in ethyl acetate and filtered through a short silica gel pad. The filtrate is concentrated and the crude product is purified by preparative TLC (eluted with 100% ethyl acetate) to give the title compound. m/e$^+$ for C$_{64}$H$_{113}$N$_{11}$O$_{12}$ 1227.86, found 1228.86(m+H)$^+$, 1250.82 (m+Na)$^+$.

Example 6

A Compound of Formula I, wherein Q is

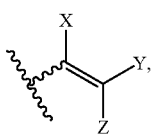

Y is —(CH$_2$)$_3$CH$_3$, and W=X=Z=hydrogen

A solution of diene acetate from Example 2 (56 mg, 0.045 mmol), 1-hexene (0.05 ml, 0.594 mmol) and Hoveyda-Grubbs' catalyst (21 mg, 0.033 mmol) in CH$_2$Cl$_2$ (2.0 ml) is degassed twice and then heated under N$_2$ at 45° C. overnight. After cooling to room temperature, solvent is removed and the product is purified by preparative TLC (developed with 100% ethyl acetate). m/e$^+$ for C$_{68}$H$_{119}$N$_{11}$O$_{13}$ 1297.90, found 1298.92 (m+H)$^+$, 1315.96 (m+NH$_4$)$^+$, 1320.91 (m+Na)$^+$, $^1$H-NMR, C-NMR and DEPT experiments indicated one diene isomer (>90%) is formed. The acetyl protection group is removed by stirring with K$_2$CO$_3$ (12.9 mg) in MeOH (2 ml) over night. After removal of methanol, the residue is dissolved in ethyl acetate and filtered through a short silica gel pad. Evaporation of solvent provided the title compound diene alcohol. m/e$^+$ for C$_{66}$H$_{117}$N$_{11}$O$_{12}$ 1255.89, found 1256.93 (m+H)$^+$, 1278.91 (m+Na)$^+$.

Example 7

A Compound of Formula I wherein Q is

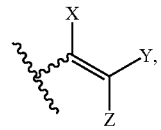

Y is —(CH$_2$)$_2$Br, and W=X=Z=hydrogen

A solution of diene acetate from Example 2 (56 mg, 0.045 mmol), 4-bromo-but-1-ene (0.05 ml,) and Hoveyda-Grubbs' catalyst (17.7 mg) in CH$_2$Cl$_2$ (2.0 ml) is heated under N$_2$ at 49° C. overnight. Mass spectrometry analysis indicated that the reaction is complete. After cooling to room temperature, solvent is removed and the product is purified by preparative TLC (developed with 100% ethyl acetate. m/e$^+$ for C$_{66}$H$_{114}$BrN$_{11}$O$_{13}$ 1347.78, found 1348,66, 1349.66, 1350.66, 1351.65 (m+H)$^+$, 1365.68, 1366.68, 1367.69, 1368.69 (m+NH$_4$)$^+$, 1370.66, 1371.66, 1372.65, 1373.65 (m+Na)$^+$. $^1$H-NMR analysis indicated one diene isomer (>90%) is formed. The acetyl protection group is removed by stirring with K$_2$CO$_3$ (12.9 mg) in MeOH (2 ml) over night. After removal of methanol, the residue is dissolved in ethyl acetate and filtered through a short silica gel pad. Evaporation of solvent provided the title compound diene alcohol. m/e for C$_{66}$H$_{114}$BrN$_{11}$O$_{13}$ 1347.78, found 1348,66, 1349.66, 1350.66, 1351.65 (m+H)$^+$, 1365.68, 1366.68, 1367.69, 1368.69 (m+NH$_4$)$^+$, 1370.66, 1371.66, 1372.65, 1373.65 (m+Na)$^+$.

Example 8

A Compound of Formula I, wherein Q is

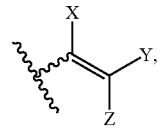

Y is ortho-Me-phenyl, and W=X=Z=hydrogen

A solution of diene acetate from Example 2 (47.8 mg), ortho-methylstyrene (0.05 ml,) and Hoveyda-Grubbs' catalyst (2.7 mg) in CH$_2$Cl$_2$ (2.0 ml) is heated under N$_2$ at 45° C. overnight. Mass spectrometry analysis indicates that the reaction is complete. After cooling to room temperature, solvent is removed and the product is purified by preparative TLC (developed with 100% ethyl acetate. m/e⁺ for $C_{71}H_{117}N_{11}O_{13}$ 1331.88, found 1332.84 (m+H)⁺, 1349.86 (m+H$_4$)⁺, 1354.82 (m+Na)⁺. The acetyl protection group is removed by stirring with $K_2CO_3$ (12.9 mg) in MeOH (2 ml) over night. After removal of methanol, the residue is dissolved in ethyl acetate and filtered through a short silica gel pad. The crude product is purified by preparative TLC (developed with ethyl acetate). m/e⁺ for $C_{69}H_{115}N_{11}O_{12}$ 1289.87, found 1290.68 (m+H)⁺, 1312.66 (m+Na)⁺.

Example 9

A Compound of Formula I, wherein Q is

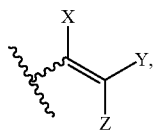

Y is ortho-Br-phenyl, and W=X=Z=hydrogen

A solution of diene acetate from Example 2 (28 mg), ortho-bromostyrene (20 ml) and Hoveyda-Grubbs' catalyst (1.4 mg) in $CH_2Cl_2$ (2.0 ml) is heated under $N_2$ at 45° C. overnight. Mass spectrometry analysis indicated that the reaction is complete. After cooling to room temperature, solvent is removed and the product is purified by preparative TLC (developed with 100% ethyl acetate. The acetyl protection group is removed by stirring with $K_2CO_3$ (12.9 mg) in MeOH (2 ml) over night. After removal of methanol, the residue is dissolved in ethyl acetate and filtered through a short silica gel pad. The crude product is purified by preparative TLC (developed with ethyl acetate). m/e⁺ for $C_{68}H_{112}BrN_{11}O_{12}$ 1355.59, found 1378.54 (m+Na)⁺.

Example 10

A Compound of Formula I, wherein Q is

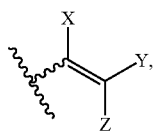

Y is —$CO_2$Me, and W=X=Z=hydrogen

A solution of diene acetate from Example 2 (27.5 mg), dimethylmaleate (32.8 mg) and Nolan catalyst (2.7 mg) in $CH_2Cl_2$ (2.0 ml) is cooled to −78° C. Then the mixture is heated under $N_2$ at 50° C. overnight. Mass spectrometry analysis indicated that the reaction is complete. After cooling to room temperature, solvent is removed and the product is purified by preparative TLC (developed with 100% ethyl acetate. m/e⁺ for $C_{66}H_{113}N_{11}O_{15}$ 1299.84, found 1300.80 (m+H)⁺, 1317.84 (m+NH$_4$)⁺, 1322.81 (m+Na)⁺. The acetyl protection group is removed by stirring with $K_2CO_3$ (12.9 mg) in MeOH (2 ml) over night. After removal of methanol, the residue is dissolved in ethyl acetate and filtered through a short silica gel pad. The crude product is purified by prepara-tive TLC (developed with ethyl acetate). m/e⁺ for $C_{64}H_{111}N_{11}O_{12}$4 1257.83, found 1296.58 (m+K)⁺, 1283.61 (m+Na)⁺.

Example 11

A Compound of Formula I, wherein Q is

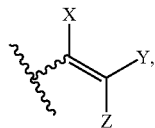

Y is meta-CHO-phenyl, and W=X=Z=hydrogen

A solution of diene acetate from Example 2 (28 mg), 3-vinylbenzaldehyde (0.015 ml,) and Hoveyda-Grubbs' catalyst (1.4 mg) in $CH_2Cl_2$ (2.0 ml) is heated under $N_2$ at 45° C. overnight. Mass spectrometry analysis indicated that the reaction is complete. After cooling to room temperature, solvent is removed and the product is purified by preparative TLC (developed with 100% ethyl acetate. m/e⁺ for $C_{71}H_{115}N_{11}O_{14}$ 1345.86, found 1346.70 (m+H)⁺, 1368.69 (m+Na)⁺. The acetyl protection group is removed by stirring with $K_2CO_3$ (12.9 mg) in MeOH (2 ml) over night. After removal of methanol, the residue is dissolved in ethyl acetate and filtered through a short silica gel pad. The crude product is purified by preparative TLC (developed with ethyl acetate). m/e⁺ for $C_{69}H_{113}N_{11}O_{13}$ 1303.85, found 1304.66 (m+H)⁺, 1326.65 (m+Na)⁺, 1342.62 (m+K)⁺.

Example 12

A Compound of Formula I, wherein Q is

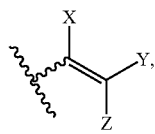

Y is Et, and W=X=Z=hydrogen

A solution of diene acetate from Example 2 (43 mg), 3-hexene(cis, trans-mixture) (0.10 ml,) and Hoveyda-Grubbs' catalyst (2.5 mg) in $CH_2Cl_2$ (1.0 ml) is heated under $N_2$ at 45° C. overnight. Mass spectrometry analysis indicates that the reaction is complete. After cooling to room temperature, solvent is removed and the product is purified by preparative TLC (Whatman, PK5F, Silica gel, 150 A, with fluorescent indicator, 500 μM thickness, developed with 100% ethyl acetate). m/e⁺ for $C_{66}H_{115}N_{11}O_{13}$ 1269.87, found 1270.73 (m+H)⁺, 1287.76 (m+NH$_4$)⁺, 1292.72 (m+Na)⁺. The acetyl protection group is removed by stirring with $K_2CO_3$ (12.9 mg) in MeOH (2 ml) at 50° C. for 1 hr. After removal of methanol, the residue is dissolved in ethyl acetate and filtered through a short silica gel pad. The crude product is purified by preparative TLC (developed with ethyl acetate). m/e⁺ for $C_{64}H_{113}N_{11}O_{12}$ 1227.86, found 1228.84 (m+H)⁺, 1250.86 (m+Na)⁺, 1266.85 (m+K)⁺.

Example 13

A Compound of Formula I, wherein Q is

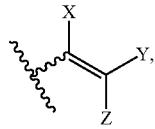

Y is —CH=CHCH$_2$TMS, and W=X=Z=hydrogen

A solution of diene acetate from Example 2 (68 mg), allyltrimethylsilane (0.10 ml,) and Hoveyda-Grubbs' catalyst (3.5 mg) in CH$_2$Cl$_2$ (1.0 ml) is heated under N$_2$ at 45° C. overnight. Mass spectrometry analysis indicated that the reaction is complete. After cooling to room temperature, solvent is removed and the product is purified by preparative TLC (Whatman, PK5F, Silica gel, 150 A, with fluorescent indicator, 500 µM thickness, developed with 100% ethyl acetate). m/e$^+$ for C$_{68}$H$_{121}$N$_{11}$O$_{13}$Si 1327.89, found 1328.88 (m+H)$^+$, 1345.88 (m+H$_4$)$^+$, 1350.88 (m+Na)$^+$. The acetyl protection group is removed by stirring with K$_2$CO$_3$ (12.9 mg) in MeOH (2 ml) at 50° C. for 1 hr. After removal of methanol, the residue is dissolved in ethyl acetate and filtered through a short silica gel pad. The crude product is purified by preparative TLC (developed with ethyl acetate). m/e$^+$ for C$_{66}$H$_{119}$N$_{11}$O$_{12}$Si 1285.88, found 1286.76 (m+H)$^+$, 1303.xx (m+NH$_4$)$^+$, 1308.80 (m+Na)$^+$, 1324.84 (m+K)$^+$.

Example 14

A Compound of Formula I, wherein Q is

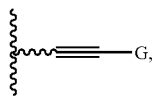

G is H, and W is H

Step a. A Compound of Formula I wherein A is of the Formula (4-2) G=TMS, and W=Ac To a solution n-BuLi (0.65 ml, 2.5 M/THF) in THF (2 ml) at −78° C. is added trimethylsilylacetylene (0.25 ml). The mixture is stirred for 10 min and a solution of cyclosporine adehyde of Example 1 (222 mg, 0.18 mmol) in THF (1 ml) is added. After addition, the mixture is stirred for 20-30 min and quenched with aq. NH$_4$Cl at −78° C. After warming to room temperature, the mixture is diluted with ethyl acetate (50 ml), washed with sat. NH$_4$Cl (30 ml), brine (30 ml), dried with Na$_2$SO$_4$, concentrated and dried by lyophilization. m/e$^+$ for C$_{67}$H$_{119}$N$_{11}$O$_{14}$Si 1329.87, found 1330,87 (m+H)$^+$, 1347.85 (m+NH$_4$)$^+$, 1352.87(m+Na)$^+$.

Step b. A Compound of Formula I, wherein A is of the Formula (4-4) G=TMS, and W=Ac To solution of the crude product from step a (100 mg) in CH$_2$Cl$_2$ (2 ml) at 0° C. is added 2,6-lutidine (0.2 ml) and triflic anhydride (0.10 ml). The mixture is stirred at 0° C. for 10 min. The mixture is diluted with ethyl acetate (20 ml), washed with brine and dried with Na2SO4. The crude product is purified by preparative TLC (developed with ethyl acetate). m/e for C$_{67}$H$_{117}$N$_{11}$O$_{13}$Si 1311.86, found 1313.04 (m+H)$^+$, 1330.06 (m+NH$_4$)$^+$, 1335.03 (m+Na)$^+$.

Step c. A Compound of Formula I, wherein Q is

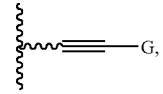

G is H, and W is H

The product from step c is heated with K$_2$CO$_3$ (20 mg) in MeOH (2 ml) at 50° C. for 1 hr. After cooling to room temperature, the solvent is removed and subsequently the residue is dissolved in ethyl acetate, washed with brine and dried with Na$_2$SO$_4$. The crude product is purified by preparative TLC (developed with ethyl acetate). m/e$^+$ for C$_{62}$H$_{107}$N$_{11}$O$_{12}$ 1197.81, found 1199.04 (m+H)$^+$, 1217.07 (m+NH$_4$)$^+$, 1221.01 (m+Na)$^+$.

Other Representative Compounds of the Present Invention which may be Prepared via the Synthetic Routes Delineated Herein Include, but are not Limited to, Examples 15-27:

Example 15

A Compound of Formula I, wherein Q is

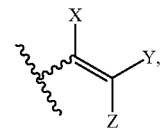

Y is propyl, and W=X=Z=hydrogen

Example 16

A Compound of Formula I, wherein Q is

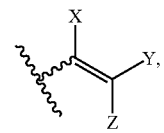

Y is cyclopropyl, and W=X=Z=hydrogen

Example 17

A Compound of Formula I, wherein Q is

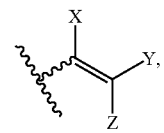

Y is —CH=CHCH$_3$, and W=X=Z=hydrogen

Example 18

A Compound of Formula I, wherein Q is

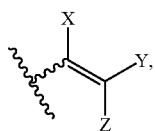

X=Y=CH₃, and W Z=hydrogen

Example 19

A Compound of Formula I, wherein Q is

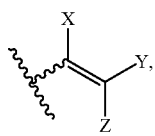

W=X=Y=hydrogen, and Z=CH₃

Example 20

A Compound of Formula I, wherein Q is

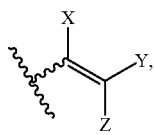

Y is p-bromophenyl, and W=X=Z=hydrogen

Example 21

A Compound of Formula I, wherein Q is

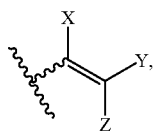

W=X=Y=hydrogen, and Z=—CH₂CH=CH₂

Example 22

A Compound of Formula I, wherein Q is

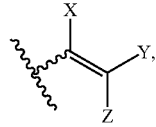

W=X=Y=hydrogen, and Z is ethyl

Example 23

A Compound of Formula I, wherein Q is

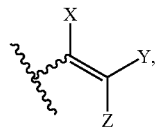

W=X=Y=hydrogen, and Z=—CH=CHCH₃

Example 24

A Compound of Formula I, wherein Q is

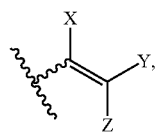

W=X=Y=hydrogen, and Z=—CH₂OCH₃

Example 25

A Compound of Formula I, wherein Q is

G=—CH=CHCH₃ and W=hydrogen

Example 26

A Compound of Formula I, wherein Q is

G=propyl and W=hydrogen

Example 27

A Compound of Formula I, wherein Q is

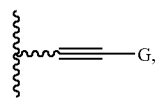

G=—CH₃ and W=hydrogen

Although the invention has been described with respect to various preferred embodiments, it is not intended to be limited thereto, but rather those skilled in the art will recognize that variations and modifications may be made therein which are within the spirit of the invention and the scope of the appended claims.

What is claimed is:

1. A compound of formula I or a pro-drug, or an ester or a pharmaceutically acceptable salt thereof:

and

A is of the formula:

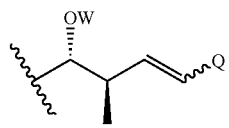

wherein:

Q is

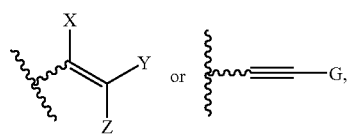

where i) X is selected from hydrogen, halogen, $C_1$-$C_6$ alkyl, or aryl;

ii) one of Y and Z is selected from: hydrogen, deuterium, halogen, or methyl and the other is independently selected from:

a) halogen;

b) $R_1$, where $R_1$ is selected from:
 1) hydrogen;
 2) deuterium;
 3) $C_1$-$C_6$ alkyl, optionally substituted with halogen, TMS, aryl, heterocycloalkyl, or heteroaryl;
 4) $C_2$-$C_6$ alkenyl, optionally substituted with halogen, TMS, aryl, heterocycloalkyl, or heteroaryl;
 5) $C_2$-$C_6$ alkynyl, optionally substituted with halogen, TMS, aryl, heterocycloalkyl, or heteroaryl;
 6) $C_3$-$C_{12}$ cycloalkyl;
 7) substituted $C_3$-$C_{12}$ cycloalkyl;
 8) aryl;
 9) substituted aryl;
 10) heterocycloalkyl;
 11) substituted heterocycloalkyl;
 12) heteroaryl; or
 13) substituted heteroaryl;

c) —C(O)OR₁, where R₁ is as previously defined;

d) —C(O)OCH₂—V—R₁, where R₁ is as previously defined and V is —O— or —S—;

e) —C(O)N(R₃)(R₄), where R₃ and R₄ are independently selected from R₁ as previously defined;

f) —C(O)SR₁, where R₁ is as previously defined;

g) —C(O)OCH₂OC(O)R₁, where R₁ is as previously defined;

h) —C(S)OR₁, where R₁ is as previously defined;

i) —C(S)SR₁, where R₁ is as previously defined;

j) R₂, where R₂ is selected from:

1) $C_1$-$C_6$ alkyl-M-R₁, where R₁ is as previously defined and M is absent or selected from:
  i. —NH—;
  ii. —N(CH₃)—;
  iii. —S—;
  iv. —S(O)ₙ—, where n=0, 1, or 2; or
  v. —O—;
 2) $C_2$-$C_6$ alkenyl-M-R₁, where R₁ and M are as previously defined; or
 3) $C_2$-$C_6$ alkynyl-M-R₁, where R₁ and M are as previously defined;

k) Or in the alternative, Y and Z are taken together with the carbon atom to which they are attached to form a $C_3$-$C_{12}$ cycloalkyl moiety; and iii) G is independently selected from halogen, TMS, R₁ or R₂ as previously defined;

B is selected from:

i) -αAbu-;

ii) -Val-;

iii) -Thr-; or iv) -Nva-;

U is selected from:

i) -(D)Ala-;

ii) -(D)Ser-;

iii) -[O-(2-hydroxyethyl)(D)Ser]-;

iv) -[O-(acyl)(D)Ser]-; or v) -[O-(2-acyloxyethyl)(D)Ser]-; and

W is selected from hydrogen or a hydroxy protecting group.

2. A compound of formula I according to claim 1, wherein A is of the formula A1:

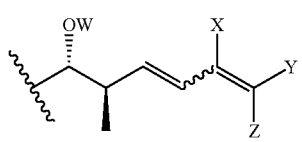
(A1)

where:
  i) X is selected from hydrogen, halogen, or $C_1$-$C_6$ alkyl;
  ii) one of Y and Z is selected from: hydrogen, deuterium, halogen, or methyl and the other is independently selected from:
    a) halogen;
    b) $R_1$, where $R_1$ is selected from:
      1) hydrogen;
      2) deuterium;
      3) $C_1$-$C_6$ alkyl, optionally substituted with halogen;
      4) $C_2$-$C_6$ alkenyl, optionally substituted with halogen; or
      5) $C_2$-$C_6$ alkynyl, optionally substituted with halogen;
    c) —C(O)O$R_1$, where $R_1$ is as previously defined;
    d) —C(O)OCH$_2$—V—$R_1$, where $R_1$ is as previously defined and V is —O— or —S—;
    e) —C(O)N($R_3$)($R_4$), where $R_3$ and $R_4$ are independently selected from $R_1$ as previously defined;
    f) —C(O)S$R_1$, where $R_1$ is as previously defined;
    g) —C(O)OCH$_2$OC(O)$R_1$, where $R_1$ is as previously defined;
    h) —C(S)O$R_1$, where $R_1$ is as previously defined;
    i) —C(S)S$R_1$, where $R_1$ is as previously defined;
    j) $R_2$, where $R_2$ is selected from:
      1) $C_1$-$C_6$ alkyl-M-$R_1$, where $R_1$ is as previously defined and M is absent or selected from:
        i. —NH—;
        ii. —N(CH$_3$)—;
        iii. —S—;
        iv. —S(O)$_n$—, where n=0, 1, or 2; or
        v. —O—;
      2) $C_2$-$C_6$ alkenyl-M-$R_1$, where $R_1$ and M are as previously defined; or
      3) $C_2$-$C_6$ alkynyl-M-$R_1$, where $R_1$ and M are as previously defined;
    k) Or in the alternative, Y and Z are taken together with the carbon atom to which they are attached to form a $C_3$-$C_{12}$ cycloalkyl moiety; and
  iii) G is independently selected from halogen, TMS, $R_1$ or $R_2$ as previously defined;
B is selected from:
  v) -αAbu-;
  vi) -Val-;
  vii) -Thr-; or
  viii) -Nva-;
U is selected from:
  vi) -(D)Ala-;
  vii) -(D)Ser-;
  viii) -[O-(2-hydroxyethyl)(D)Ser]-;
  ix) -[O-(acyl)(D)Ser]-; or
  x) -[O-(2-acyloxyethyl)(D)Ser]-; and
W is selected from hydrogen or a hydroxy protecting group.
  3. A compound of formula I according to claim 2, wherein A is of the formula A2:

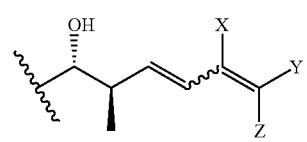
(A2)

where X, Y, and Z are as defined in claim 2.
  4. A compound of formula I according to claim 2, wherein A is of the formula A3:

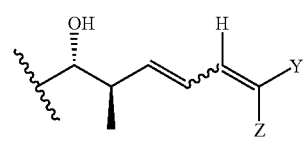
(A3)

where Y and Z are as defined in claim 2.
  5. A compound of formula I according to claim 1, wherein A is of the formula A4:

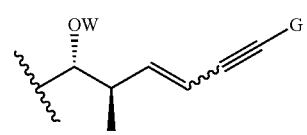
(A4)

where W and G are as defined in claim 1.
  6. A compound of formula I according to claim 1, wherein A is of the formula A5:

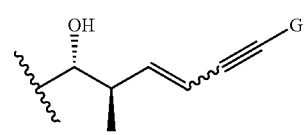
(A5)

where G is as defined in claim 1.
  7. A compound of formula I, according to claim 1, selected from:
Example 2: A compound of formula I, wherein Q is

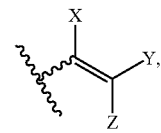

W is Ac and X=Y=Z=hydrogen;
Example 3: A compound of formula I, wherein Q is

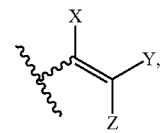

W is H and X=Y=Z=hydrogen;

Example 4: A compound of formula I, wherein Q is

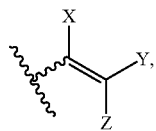

Y is CH$_3$, and W=X=Z=hydrogen;
Example 5: A compound of formula I, wherein Q is

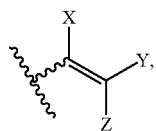

Y=Z=CH$_3$, and W=X=hydrogen;
Example 6: A compound of formula I, wherein Q is

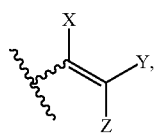

Y is —(CH$_2$)$_3$CH$_3$, and W=X=Z=hydrogen;
Example 7: A compound of formula I, wherein Q is

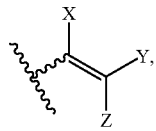

Y is —(CH$_2$)$_2$Br, and W=X=Z=hydrogen;
Example 10: A compound of formula I, wherein Q is

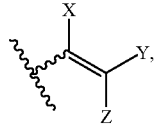

Y is —CO$_2$Me, and W=X=Z=hydrogen;
Example 12: A compound of formula I, wherein Q is

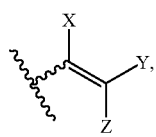

Y is Et, and W=X=Z=hydrogen;

Example 13: A compound of formula I, wherein Q is

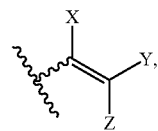

Y is —CH=CHCH$_2$TMS, and W=X=Z=hydrogen;
Example 14: A compound of formula I, wherein Q is

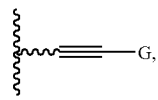

G is H, and W is H;
Example 15: A compound of formula I, wherein Q is

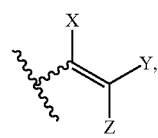

Y is propyl, and W=X=Z=hydrogen;
Example 16: A compound of formula I, wherein Q is

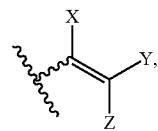

Y is cyclopropyl, and W=X=Z=hydrogen;
Example 17: A compound of formula I, wherein Q is

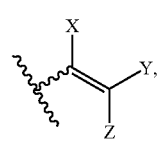

Y is —CH=CHCH$_3$, and W=X=Z=hydrogen;
Example 18: A compound of formula I, wherein Q is

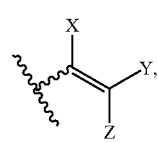

X=Y=CH$_3$, and W=Z=hydrogen;

Example 19: A compound of formula I, wherein Q is

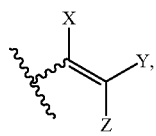

W=X=Y=hydrogen, and Z=CH₃;

Example 21: A compound of formula I, wherein Q is

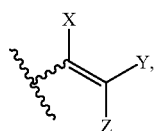

W=X=Y=hydrogen, and Z=—CH₂CH=CH₂;

Example 22: A compound of formula I, wherein Q is

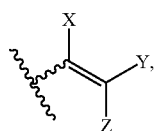

W=X=Y=hydrogen, and Z is ethyl;

Example 23: A compound of formula I, wherein Q is

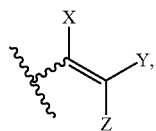

W=X=Y=hydrogen, and Z=—CH=CHCH₃;

Example 24: A compound of formula I, wherein Q is

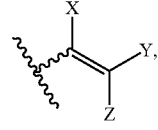

W=X=Y=hydrogen, and Z=—CH₂OCH₃;

Example 25: A compound of formula I, wherein Q is

G=—CH=CHCH₃ and W=hydrogen;

Example 26: A compound of formula I, wherein Q is

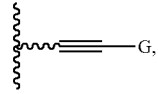

G=propyl and W=hydrogen; or

Example 27: A compound of formula I, wherein Q is

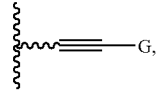

G=—CH₃ and W=hydrogen.

8. A pharmaceutical composition comprising at least one compound of Formula (I) in claim 1, or a pharmaceutically acceptable salt, ester or prodrug thereof, in combination with a pharmaceutically acceptable carrier or excipient.

\* \* \* \* \*